United States Patent
Olson et al.

(10) Patent No.: US 11,432,739 B2
(45) Date of Patent: Sep. 6, 2022

(54) MAGNETIC FIELD DISTORTION DETECTION AND CORRECTION IN A MAGNETIC LOCALIZATION SYSTEM

(71) Applicant: St. Jude Medical International Holding S.á r.l., Luxembourg (LU)

(72) Inventors: Eric S. Olson, Maplewood, MN (US); Alon Izmirli, Ganot Hadar (IL); Guy Hevel, Zicron Yaakov (IL)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 306 days.

(21) Appl. No.: 16/097,678

(22) PCT Filed: May 3, 2017

(86) PCT No.: PCT/IB2017/052576
§ 371 (c)(1),
(2) Date: Oct. 30, 2018

(87) PCT Pub. No.: WO2017/191578
PCT Pub. Date: Nov. 9, 2017

(65) Prior Publication Data
US 2020/0359932 A1  Nov. 19, 2020

Related U.S. Application Data

(60) Provisional application No. 62/331,338, filed on May 3, 2016.

(51) Int. Cl.
*A61B 5/06* (2006.01)
*A61B 34/20* (2016.01)
*A61B 5/00* (2006.01)

(52) U.S. Cl.
CPC ............ *A61B 5/062* (2013.01); *A61B 5/7253* (2013.01); *A61B 34/20* (2016.02); *A61B 2034/2051* (2016.02); *A61B 2562/0223* (2013.01)

(58) Field of Classification Search
CPC ....... A61B 5/062; A61B 34/20; A61B 5/7253; A61B 2034/2051; A61B 2562/0223
See application file for complete search history.

(56) References Cited

U.S. PATENT DOCUMENTS

| | | | |
|---|---|---|---|
| 6,147,480 A * | 11/2000 | Osadchy | A61B 5/06 324/67 |
| 6,400,139 B1 * | 6/2002 | Khalfin | G01S 1/024 324/207.12 |

(Continued)

FOREIGN PATENT DOCUMENTS

EP    1887309 A1    2/2008

OTHER PUBLICATIONS

Bookstein, Fred L. "Principal warps: Thin-plate splines and the decomposition of deformations." IEEE Transactions on pattern analysis and machine intelligence 11.6 (1989): 567-585. (Year: 1989).*

(Continued)

*Primary Examiner* — Sean D Mattson
(74) *Attorney, Agent, or Firm* — Dykema Gossett PLLC

(57) ABSTRACT

Various embodiments of the present disclosure identify and correct for magnetic field distortions within a magnetic field for localization of a medical device within a patient. Such magnetic field distortions, often associated with the intrusion of a metallic object into the magnetic field, may cause an unacceptable level of localization error which aspects of the present disclosure correct for.

14 Claims, 10 Drawing Sheets

(56) References Cited

U.S. PATENT DOCUMENTS

| | | | |
|---|---|---|---|
| 6,690,963 B2* | 2/2004 | Ben-Haim | A61N 1/36564 600/117 |
| 7,902,816 B2* | 3/2011 | Shechter | A61B 5/062 324/207.12 |
| 2004/0102696 A1* | 5/2004 | Govari | A61B 5/06 600/424 |
| 2004/0254453 A1 | 12/2004 | Govari | |
| 2005/0107687 A1 | 5/2005 | Anderson | |
| 2006/0122497 A1* | 6/2006 | Glossop | A61B 34/20 600/424 |
| 2008/0157755 A1* | 7/2008 | Kruger | A61B 34/20 324/207.12 |
| 2008/0183064 A1 | 7/2008 | Chandonnet | |
| 2008/0221425 A1* | 9/2008 | Olson | A61B 90/36 600/407 |
| 2009/0048509 A1* | 2/2009 | Wu | A61B 90/36 600/424 |
| 2009/0082989 A1* | 3/2009 | Zuhars | G01B 7/003 702/150 |
| 2010/0168556 A1* | 7/2010 | Shen | A61B 5/062 600/424 |
| 2010/0331671 A1 | 12/2010 | Martinelli et al. | |
| 2011/0156700 A1 | 6/2011 | Kariv | |
| 2012/0092004 A1 | 4/2012 | Billeres et al. | |
| 2014/0354300 A1* | 12/2014 | Ramachandran | G01R 23/00 324/654 |

OTHER PUBLICATIONS

Fasshauer, Gregory E. Meshfree approximation methods with MATLAB. vol. 6. World Scientific, 2007. (Year: 2007).*

Japanese Patent Office, Notification of Reasons for Rejection in counterpart Japanese patent application No. 2019-234517, dated Apr. 13, 2021.

European Patent Office, Extended European Search Report in counterpart European application No. 20188160.4-1113, dated Feb. 15, 2021.

* cited by examiner

US 11,432,739 B2

MAGNETIC FIELD DISTORTION DETECTION AND CORRECTION IN A MAGNETIC LOCALIZATION SYSTEM

CROSS-REFERENCE TO RELATED APPLICATION

This application is the National Stage of International Application No. PCT/IB132017/052576, filed 3 May 2017, which claims the benefit of United States provisional application no. 62/331,338, filed 3 May 2016, which are hereby incorporated by reference as though fully set forth herein.

BACKGROUND a. Field

The present disclosure relates generally to the magnetic localization of medical instruments within a patient. More specifically, the instant disclosure relates to detecting and correcting for magnetic field distortions within a magnetic field used for magnetic localization.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature to the intended site, for example, a site within the patient's heart, and carries one or more electrodes, which may be used for diagnosis, mapping, ablation, or other treatments. Precise positioning of the catheters and clinician knowledge of the precise location within the body of the patient is desirable for improved procedure efficacy.

To position a catheter within the body at a desired site, some type of navigation must be used, such as using mechanical steering features incorporated into the catheter (and/or into an introducer sheath). To determine the relative position of the catheter to patient anatomy, magnetic localization systems have been developed that provide a location of the catheter within an artificially created magnetic field. The externally generated magnetic field includes precise magnetic gradients (field lines) that are unique at every location within the field. The catheter, while within the magnetic field, senses the unique magnetic field at its location (e.g., by elements such as coils). The magnetic field detected by the catheter is then algorithmically processed to determine the position of the catheter within patient as desired, a clinician may operate the catheter, for example, to ablate tissue to interrupt potentially pathogenic heart rhythms.

However, magnetic localization systems are susceptible to error induced by magnetic distortions within the magnetic field caused by, for example, extraneous ferrous or metallic objects intruding into the magnetic field. The introduction of such distortions may result in the system presenting an inaccurate position of the catheter within the patient's body. Such inaccurate catheter location data can limit the efficacy of a medical procedure.

The foregoing discussion is intended only as an exemplary illustration of the present field and is not intended to limit the claim scope.

BRIEF SUMMARY

Various embodiments of the present disclosure identify and correct for magnetic field distortions within a magnetic field for localization of a medical device within a patient. Magnetic field distortions, often associated with the intrusion of a metallic object into the magnetic field, may cause an unacceptable level of error in localizing the medical device within the patient. In particular, the instant disclosure relates to various systems apparatuses, and computer programs for detection and correction of such magnetic distortions, which allow for the accurate localization of the medical device within the patient regardless of magnetic distortions within the magnetic field.

In one embodiment of the present disclosure, a system is disclosed for detecting and correcting for magnetic distortions in a magnetic field for localizing a medical device within a patient positioned within the magnetic field. The system includes a magnetic field emitter with one or more emitter coils at known positions and orientations within the system. Each of the emitter coils emit a unique magnetic field relative to the other emitter coils in the magnetic field emitter. The system further includes one or more medical device sensor coils which sense the magnetic field proximate thereto, and outputs a first electrical signal indicative of the sensed magnetic field at the medical device. An array of magnetic distortion sensors are located at known positions and orientations within the system. Each of the magnetic distortion sensors sense the magnetic field proximate thereto, and output a second electrical signal indicative of the sensed magnetic field at the magnetic distortion sensor. Processor circuitry, communicatively coupled to each of the magnetic distortion sensors and the medical device sensor coils, receives the first and second electrical signals, and determines a magnetic distortion corrected position of the medical device within the system based on the first and second electrical signals, and the known position and orientation of the magnetic distortion sensors.

In further more specific embodiments, the processor circuitry determines the magnetic distortion corrected position of the medical device by determining perceived locations of each of the magnetic distortion sensors in the array based on the sensed magnetic field at each magnetic distortion sensor. A localized error is then determined between the perceived location and the known position of each of the magnetic distortion sensors. Based on the localized error determinations, a transform is calculated that converts the perceived locations to the known locations for each of the magnetic distortion sensors. Using the calculated transform, a corrected position of the medical device within the system is determined that compensates for the magnetic distortion proximal to the medical device.

In another embodiment, a sensor array apparatus is disclosed for detecting magnetic distortions within a magnetic field. The sensor array apparatus includes a plurality of sensor coils, each of the sensor coils collect energy indicative of the magnetic field strength and orientation at the sensor coil. A non-ferrous frame is coupled to each of the plurality of sensor coils and positions and orients each of the sensor coils relative to one another and a magnetic field emitter. Processing circuitry, electrically coupled to the plurality of sensor coils, receives the signals from each of the sensor coils and conditions and processes the received signals. For example, the conditioning and processing may include one or more of the following: pre-amplification, analog-to-digital conversion, noise filtering, and signal isolation. The processed signals may be indicative of the existence of magnetic distortion within the magnetic field due to ferrous object ingress thereto.

In yet another embodiment, a computer program for correcting magnetic distortion in a magnetic field used for localization of a medical device within a patient is disclosed. The computer program includes the steps of calculating a perceived location of each of a plurality of sensor coils in a sensor array based upon a received signal at the sensor coil indicative of a magnetic field proximal the sensor coil. Based on the discrepancy between a known position of the sensor coil and the perceived location of the sensor coil, a positional error is determined for each of the plurality of sensor coils. The positional error is indicative of a magnetic distortion in the magnetic field at the sensor coil. Based on the discrepancy between the known and perceived locations of each of the sensor coils, a transform is calculated that converts the perceived locations to the known location for each of the plurality of sensor coils. Based upon a received signal at the medical device indicative of the magnetic field proximal the medical device, a perceived location of the medical device is calculated. An actual location of the medical device is determined by entering the perceived location of the medical device into the computed transform.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings.

Figure 1A:
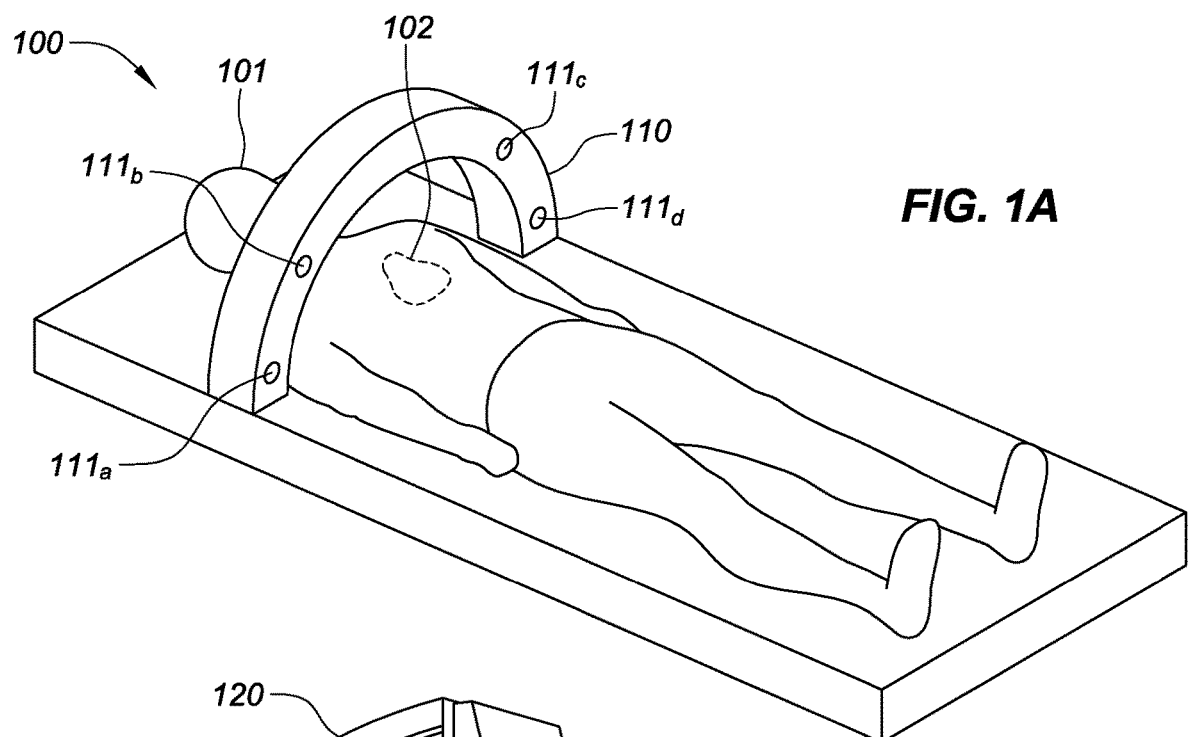
FIG. 1A is an isometric view of a magnetic distortion detection and correction system, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Various embodiments of the present disclosure identify and correct for magnetic field distortions within a magnetic field for localization of a medical device within a patient. Such magnetic field distortions, often associated with the intrusion of a metallic object into the magnetic field, may cause an unacceptable level of error in localization of the medical device within the patient. Details of the various embodiments of the present disclosure are described below with specific reference to the figures.

Cardiac Mapping Systems are capable of displaying a three-dimensional (3D) position of conventional electrophysiology catheters within an overlaid model or image of a cardiac chamber. These mapping systems may also display cardiac electrical activity as waveform traces and as dynamic 3-D isopotential maps on the model of the cardiac chamber. The contoured surfaces of these three dimensional models are based on the anatomy of the patient's own cardiac chamber. These mapping systems may use magnetic based localization technologies to render catheter position and assist in model creation.

When using magnetic localization, the magnetic fields generated from a local source are inherently susceptible to distortions caused by metallic or ferrous objects intruding into, or being placed adjacent to, the generated magnetic fields. Such distortions can cause inaccuracies in calculated or determined catheter locations and in related anatomical models and other representations.

Magnetic sensors embedded within EP catheters are used to determine position and orientation of the catheter with respect to one or more known reference positions. This magnetic position and orientation information may also be used to navigate the catheter when overlaid on a model of a cardiac chamber, for example. When navigating catheters in magnetic space, the displayed or otherwise reported positions of the catheters can notably shift (e.g., visually shift on a mapping system display showing a representation of the location of the catheter relative to the cardiac chamber) when the underlying magnetic field is changed/distorted despite no actual change (or minimal actual change) in the catheter's physical location. This type of magnetic distortion can also cause inaccuracies in the models created using the reported locations of the catheters. Embodiments of the present disclosure, as described in more detail below with reference to the figures, identify such magnetic distortions within a magnetic field and correct for those distortions when determining a position of the catheter within the patient.

FIG. 1A shows an isometric view of a magnetic localization system 100 used for navigating the human anatomy of a patient 101 while conducting a medical procedure. For example, the system may be used to map a heart 102 of the patient and to navigate a cardiac catheter 105 (as in FIG. 1B) through the chambers of the heart. Magnetic localization system 100 determines the location (and, in some embodiments, the orientation) of objects (e.g., a portion of a diagnostic or ablation catheter, such as the tip of the cardiac catheter), typically within a three dimensional space, and expresses those locations as position information determined relative to at least one reference. Specifically, the magnetic localization system 100 can be used to determine the location of the cardiac catheter 105 within a magnetic field, which is then overlaid onto, for example, an image or a model of the heart 102. In more specific embodiments, magnetic resonance imaging data, among other reference data, may be overlaid onto the three-dimensional space to provide a clinician with a virtual work environment in which to reference for real-time position of the cardiac catheter relative to the patient's heart.

The magnetic localization system 100 may include various visualization, mapping, and navigation components. For example, the localization system 100 may include a magnetic-field-based system such as the CARTO™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the localization system 100 may include a magnetic field based system such as the MEDIGUIDE™ Technology system available from St. Jude Medical, Inc., and as generally shown with reference to one or more of U.S. Pat. Nos. 6,233,476; 7,197,354; 7,386,339; and U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/IB2014/059709 entitled "Medical Device Navigation System" filed on 13 Mar. 2014, the disclosures of which are hereby incorporated by reference in their entireties as though fully set forth herein. In yet another embodiment, the localization system 100 may comprise a hybrid electric-field-based and magnetic-field-based system, such as, for example and without limitation, the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, each of which is hereby incorporated by reference in its entirety as though set forth fully herein, or the CARTO™ 3 system commercially available from Biosense Webster. In yet still other exemplary embodiments, the localization system 100 may comprise or be used in conjunction with other commonly available systems, such as, for example and without limitation, fluoroscopic, computed tomography (CT), and magnetic resonance imaging (MRI)-based systems.

A single-use catheter assembly 104 (as in FIG. 1B) may include a catheter tip assembly 105 (or an electrode assembly or distal tip assembly) at a distal end portion. The catheter tip assembly may be operatively adapted for conducting a diagnostic or a therapeutic procedure under clinician control. A proximal end portion of the catheter 105 may include a steering handle or other mechanism (not shown). In the present embodiment, catheter 105 is a mapping catheter. The catheter 105 includes a flexible shaft extending between the proximal end portion and the catheter tip assembly. The catheter assembly further includes an electrical connector (not shown) configured to establish electrical connection(s) between the catheter tip assembly and external electrical apparatus (not shown) to perform, for example, localization, mapping, ablation, and/or pacing procedures. The catheter tip assembly may comprise a plurality of localization sensor coils such as those shown in U.S. Pat. No. 6,690,963 (see, e.g., sensors 30, 32, 34 depicted in FIGS. 2 and 3), which is hereby incorporated by reference in its entirety as though fully set forth herein.

Figure 1B:
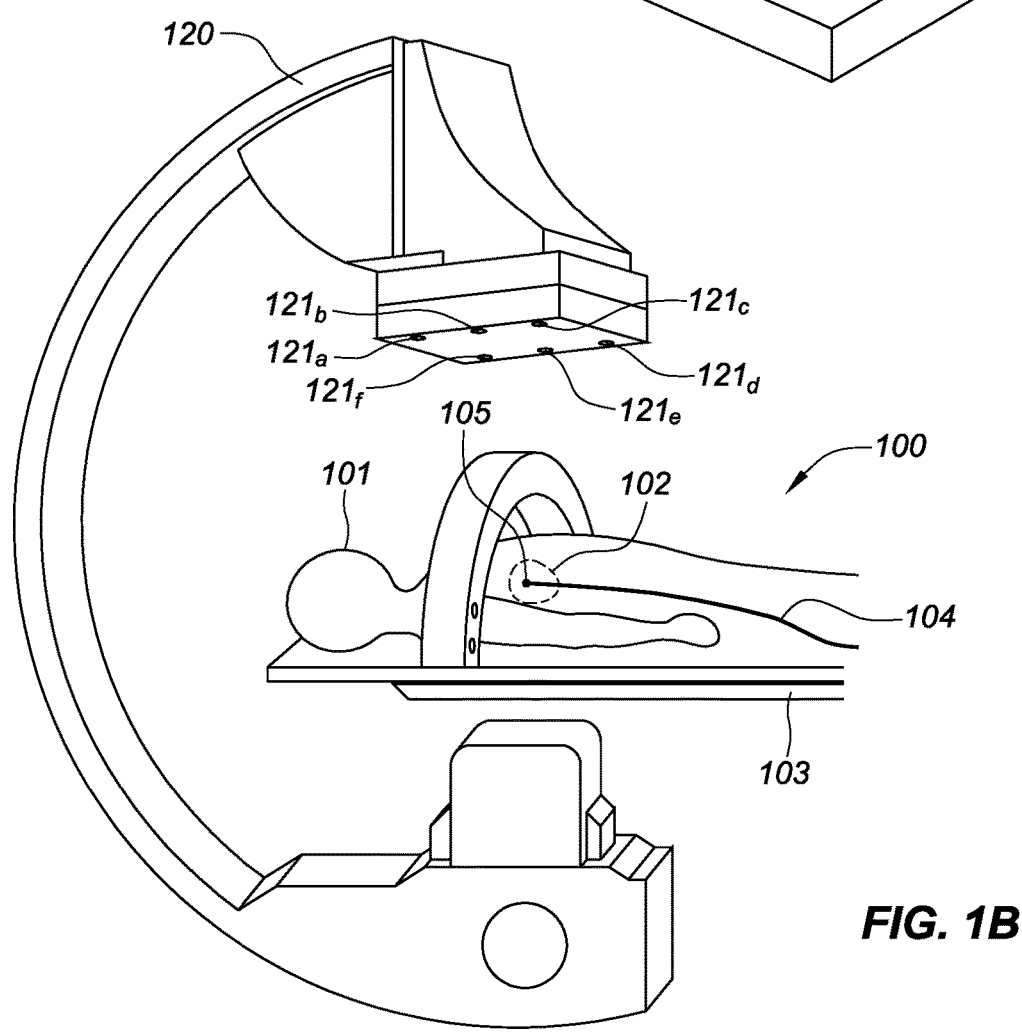
FIG. 1B is a side-view of the magnetic distortion detection and correction system of FIG. 1A with a C-arm for fluoroscopic imaging and magnetic field emission, consistent with various aspects of the present disclosure.

As shown in FIG. 1B, a magnetic localization system 100 includes a plurality of magnetic field transmitters $121_{a-f}$ in a magnetic field transmitter housing 120. In various embodiments of the present disclosure, the magnetic field transmitters may be incorporated into a fluoroscopy imaging system (referred herein as the magnetic field transmitter housing 120), such as a C-Arm; such a combination provides numerous benefits including, importantly, fluoroscopic imaging and localization data tied to the same coordinate system. Each of the magnetic field transmitters emit a magnetic field across a patient's body 101. The magnetic field defines three generally orthogonal axes, e.g., an x-axis, a y-axis, and a z-axis. The magnetic field transmitters are electrically coupled to a magnetic field generator. The magnetic field generator generates one or more magnetic fields which may be transmitted by the magnetic field transmitters simultaneously, time multiplexed, and/or frequency multiplexed. Absent any magnetic distortion, each location within the magnetic field is associated with a unique magnetic field signature including a field gradient and strength.

For a cardiac ablation procedure, by way of example, a sensor coil array 110 is positioned circumferential the patient's heart 102, and positioned below the magnetic field transmitter housing 120, and within the magnetic field emitted therefrom. In the present embodiment, the sensor coil array is affixed to operating table 103, providing a fixed (and known) location of each magnetic distortion sensor coil $111_{a-d}$ relative to the magnetic field transmitter housing. Each of the magnetic distortion sensor coils sense the magnetic field, proximate to, and substantially co-planar with an orientation of the sensor coil in the sensor coil array, and output an electrical signal indicative of the sensed magnetic field at its fixed location. As discussed above, as this received magnetic field is unique at every location within the magnetic field, the outputted electrical signal of the magnetic distortion sensor coil is indicative of the perceived location of the sensor coil within the magnetic field. However, magnetic distortions within the magnetic field may cause a discrepancy between the actual location of the sensor coil in the fixed sensor coil array and the perceived location of the sensor coil by the magnetic localization system 100.

The head of the catheter 105 includes one or more sensor coils that sense the magnetic field, proximate to, and substantially co-planar with the orientation of the sensor coil. Each of the catheter sensor coils outputs an electrical signal indicative of the sensed magnetic field at its location; which is unique to the specific location of the catheter within the magnetic field.

Outputs of magnetic distortion sensor coils $111_{a-d}$ and catheter 105 are transmitted to and sampled by processing circuitry. The processing circuitry performs computations based on the outputs of the sensor coils to determine, for example, the perceived location of a cardiac catheter within the heart. The perceived location of the cardiac catheter may be used for reference by a clinician during a procedure, and be presented to the clinician on a display in relation to known reference points, e.g., cardiac chambers, arteries, etc. However, the actual catheter position may be obscured by magnetic distortions within the magnetic field caused by other ferrous/metallic bodies. These magnetic distortions are associated with an error rate of the perceived position of the catheter compared to the actual position of the catheter.

To compensate for magnetic distortion in the magnetic localization system 100, sensor coil array 110 provides a fixed reference frame, and may define the origin of the system's coordinate frame. Based on the discrepancy between the actual position and the perceived location of each of the magnetic distortion sensors $111_{a-d}$ in the sensor coil array, the effect of the magnetic distortion throughout the magnetic field may be calculated and represented by a transform that restores the perceived locations of each of the magnetic distortion sensor coils back to the respective actual locations. Similarly, this transform may be applied to the perceived location of the catheter within the magnetic field to determine a corrected (actual) location of the catheter in view of the magnetic distortion.

As further shown in FIGS. 1A and 1B, the magnetic distortion sensors $111_{a-d}$ are placed in an arc (as defined by the sensor coil array 110) with a center-point of the arc generally located around an anatomical portion of the patient that is being operated on. The configuration of the sensor coil array may take a number of forms including an arc, a pyramid, a cube, etc. The sensor coil array may surround the chest/thorax of the patient to provide a global view of the magnetic fields. In some embodiments of the present disclosure, the legs of the sensor coil array may be longer or shorter in each dimension such that they would accommodate patients of different sizes. The legs of the sensor coil array may also surround the outside of a patient's arms, or, in the alternative, fit between the patient's arms and body. Importantly, it is desirable for the sensor coil array to be sufficiently rigid to prevent movement of the magnetic distortion sensors relative to the magnetic field emitters. In embodiments where it is advantageous to have magnetic distortion sensor beneath the patient, the magnetic distortion sensors may be designed into a fixture or mat that is placed between the patient and the operating table 103. To maximize efficacy of the magnetic localization system 100, it is recommended that the magnetic distortion sensor coils are arranged such that they span different Cartesian axes. However, an arrangement of magnetic distortion sensor coils, such as a flat mat placed beneath the patient, may still identify and correct for magnetic distortion.

Numerous additional embodiments for the arrangement of the magnetic distortion sensor coil array are possible. For example, the array may be placed on the body of the patient (or in other locations) and tracked with an independent location system such as the Polaris™ system from Northern Digital (NDI) or other visually based 3D location system. The independent location tracking system provides location data for each of the magnetic distortion sensor coils in lieu of affixing them to a rigid known frame.

In embodiments such as that presented in FIGS. 1A and 1B, the sensor coil array is roughly centered about the patient's heart 102, which is receiving treatment by way of catheter 105. The sensor coil array is desirably positioned between magnetic field transmitters $121_{a-e}$ in a magnetic field transmitter housing 120 and the patient's heart, so that magnetic distortions affecting the catheter 105 are sensed by one or more of magnetic distortion sensors $111_{a-d}$ in the sensor coil array 110. For example, during an operation the clinician may require the use of one or more operating instruments, many of which are metallic or ferrous by nature. If an operating instrument enters the magnetic field emitted by one or more of the magnetic field transmitters, the magnetic field proximate to the operating instrument will be distorted. The affect the operating instrument has on the magnetic field gradient and strength is dependent on the ferrous metal content and density of the instrument. However, even small distortions in the magnetic field may greatly impact the perceived location of the catheter within the patient's heart.

Catheter 105 includes a coil in its tip region which senses the magnetic field strength and gradient proximate the catheter tip region. As discussed above, the sensed magnetic field at the location of the catheter tip within the magnetic field is unique to that location within the magnetic field. Based on the sensed magnetic field at the tip of the catheter, processing circuitry may determine, where the coil is located in the magnetic field. This information, in conjunction with other known locations within a coordinate system (e.g., chambers, valves, and arteries) allows a clinician to navigate the catheter within the patient's heart using the (near) real-time position data provided by the magnetic localization system 100.

To prevent inaccuracies in a magnetic localization system 100, the system utilizes one or more magnetic distortion sensors $111_{a-d}$ to determine a discrepancy between actual locations (based on the known/fixed position of the magnetic distortion sensor within the system) and perceived locations (those determined based on the received magnetic fields at the magnetic distortion sensor and post-processing). The determined discrepancy is indicative of magnetic distortion throughout the magnetic field due to egress of ferrous/metallic objects into the magnetic field. Based on the discrepancy at each of the magnetic distortion sensor locations, a transform may be computed to correct for the distortion at all locations within the magnetic field. In such a system, magnetic distortions can be identified and corrected for in reference to the perceived location of the catheter. Specific algorithms for determining and correcting for the existence of magnetic distortions within the magnetic field are presented below.

Figure 2:
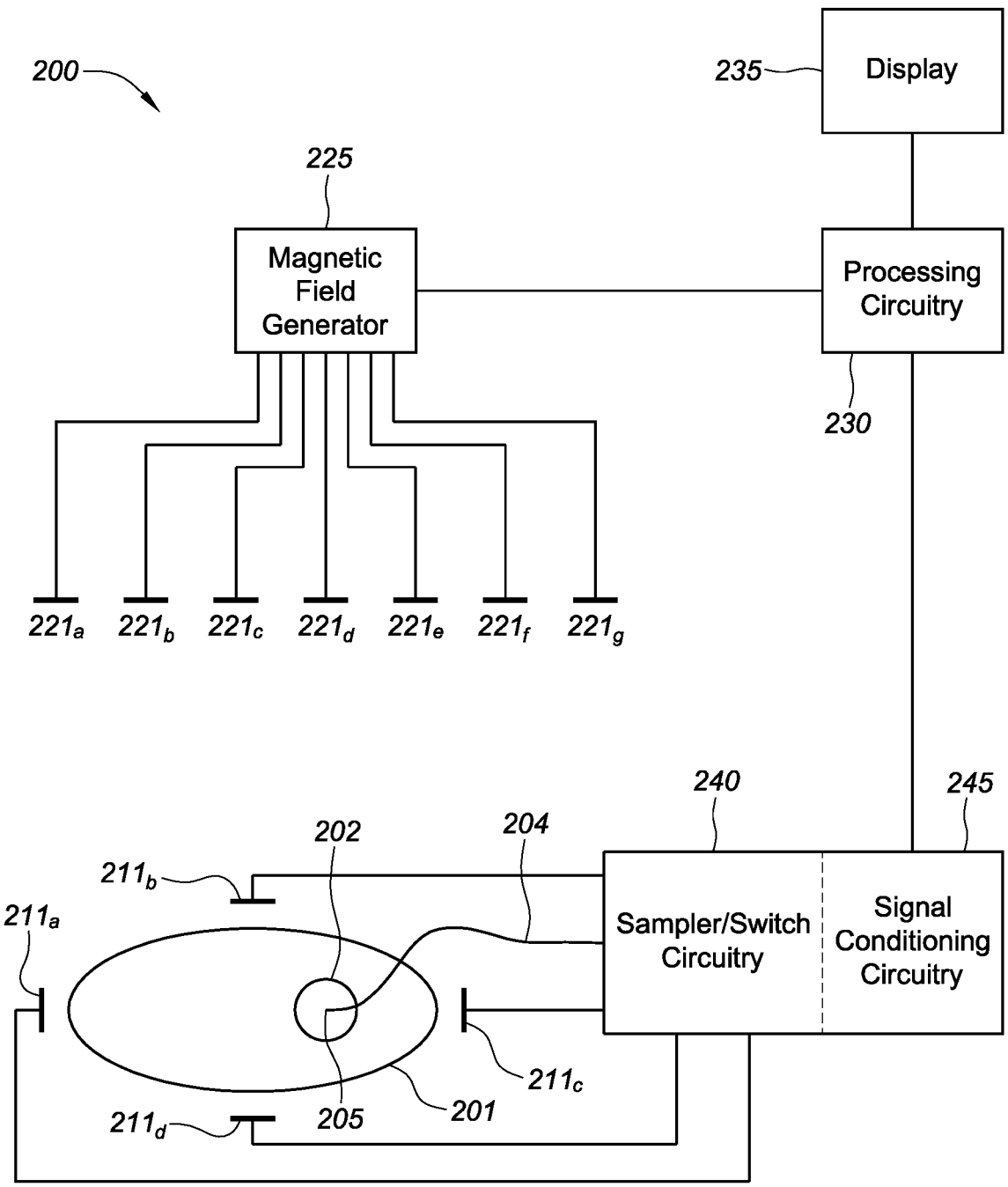
FIG. 2 is a schematic diagram of a magnetic distortion detection and correction system, consistent with various aspects of the present disclosure.

FIG. 2 is a schematic diagram of a magnetic localization system 200 with magnetic distortion detection and correction, consistent with various aspects of the present disclosure. As shown in FIG. 2, processing circuitry 230 enables a magnetic field generator 225 to produce and transmit electrical signals to each of the magnetic field transmitters $221_{a-g}$. When the electrical signal from the magnetic field generator is received by a respective magnetic field transmitter, the transmitter produces a magnetic field that emanates therefrom. In specific embodiments of the present disclosure, the magnetic field generator may independently drive each of the magnetic field transmitters with a unique electrical signal. These unique signals may be generated simultaneously, time multiplexed, frequency multiplexed, or a combination thereof. As a result, the perceived magnetic field at every location within the magnetic field is unique and therefore identifiable based on the magnetic field sensed at that location.

In one specific embodiment, magnetic field transmitters $221_{a-g}$ are generally comprised of multiple coils whose position and orientation allow for the creation of several unique magnetic fields. Fields are generated by driving a current into the coil which creates a magnetic field according to the Biot-Savart law:

$$dB = \frac{\mu_o \mu_r}{4\pi} \times \frac{Idl\sin\theta}{r^2}$$

To allow for the creation of multiple fields, the system is designed to multiplex generated fields. The magnetic distortion sensors $111_{a-d}$ are also coils (which may be less then 2 mm×10 mm in size). The magnetic fields impose a current in the magnetic distortion sensors which is proportional to field strength at the location and the orientation of the sense coil relative to the magnetic field. As a magnetic distortion sensor coil placed in a magnetic field may produce the same output for a variety of locations, it may not be possible to determine its position and orientation from a single imposed magnetic field. By providing several magnetic fields, as mentioned previously, the combination of each of the sensed currents at a given location within the emitted magnetic fields can be unique. However, it has been discovered that such magnetic localization systems are prone to error when calculating the perceived location of an object within the magnetic field when a ferrous/metallic object enters and distorts the magnetic field emitted by the magnetic field transmitters $221_{a-g}$.

Aspects of the present disclosure detect and correct for magnetic distortion within a magnetic localization system 200. In one exemplary system setup, a patient 201 is positioned within the magnetic field emitted by the magnetic field transmitters $221_{a-g}$. Ideally, the anatomy of the patient's body being operated on is centered within the magnetic field. In the present example, the patient's heart 202 is centered within the magnetic field and a catheter 204 is extended within the heart for a medical procedure. For example, catheters have been used for diagnostic, therapeutic, mapping, ablative procedures, etc. A plurality of magnetic distortion sensors $211_{a-d}$ are placed proximate to the patient's body. In an ideal configuration, magnetic distortion sensors would be evenly spaced proximate to the patient's heart 202 (or the body 201 more generally). Such placement of the magnetic distortion sensors relative to the patient's heart allows for consistent detection of magnetic distortions around the heart.

In some magnetic localization systems, however, it may be difficult to fully encompass the patient with magnetic distortion sensors $211_{a-d}$; for example, due to impeding structures (e.g., operating table) or necessary clearances (e.g., a C-Arm fluoroscopy system which requires clearance to rotate about the operating table). An x-ray detector and emitter of the C-Arm fluoroscopy system are often moved about and are composed of a significant amount of metal. Moving the C-arm can cause noticeable magnetic distortions in the magnetic field and result in erroneous location information for the catheter being tracked.

With no intervening ferrous object (the ferrous object may also be referred to as a foreign, ferrous object; examples of which may include: a C-Arm fluoroscopy system, and other capital equipment that may include ferrous material) and the C-arm parked in a default position (e.g. anterior-posterior) the magnetic field may be essentially homogeneous. As the C-arm is moved or as metal is introduced in the magnetic field, the magnetic field may be deformed. By continuously computing a transformation that restores the location of the magnetic distortion sensors to their known locations, the magnetic distortion can be corrected such that the discrepancy between the perceived and actual position of each of the magnetic distortion sensors is brought to zero. Other points in the coordinate system, such as the location of a catheter, will also be restored. The learned transformation will effectively perform an interpolation between the magnetic distortion sensor locations such that residual error can be minimized Increasing the number of magnetic distortion sensors within the system will generally improve the results.

In many embodiments, it is desirable to maintain as many magnetic distortion sensors between the magnetic field transmitters $221_{a-g}$ and a catheter tip 205 for which localization within the patient's heart 202 is desired; this is due in part to the enhanced effect of magnetic distortions proximate to the magnetic field transmitters on localization of the catheter tip within the magnetic field, relative to the effect of magnetic distortions outside of the region between the catheter tip and the magnetic field transmitters.

In operation, magnetic localization system 200 converts the magnetic field sampled at each of the magnetic distortion sensors $211_{a-d}$ and catheter tip 205 into an electrical signal; which is indicative of a magnetic field gradient and strength at the sampled location. As discussed above, the received signal for each of the magnetic distortion sensors $211_{a-d}$ and the catheter tip 205 is unique relative to the position at which it is received within the magnetic field. Sampler/switch circuitry 240 samples the electrical signals from the magnetic distortion sensors $211_{a-d}$ and the catheter tip 205 at a desired frequency.

In specific embodiments, the system may sample these electrical signals in syncopation with various stages of the heart beat as determined by an electrocardiogram, or other similar sensing means. Similarly, a C-arm fluoroscopy system (or other similar fluoroscopy imaging system) used in conjunction with the magnetic localization system 200 may image the heart 202 during the same stages of the heartbeat. The images may then be looped into a video that is displayed for the clinician during the operation. The location of the catheter tip 205 during these various stages of the heart beat may be overlaid on the fluoroscopy images to produce a video that appears to mimic real-time fluoroscopy imaging and localization of the catheter tip within the heart. Importantly, however, such an embodiment greatly decreases the x-ray radiation exposure of the patient and clinician during the operation as the C-arm fluoroscopy system need not be taking images in order for the clinician to determine the location of the catheter within the heart.

Received electrical signals from each of the magnetic distortion sensors $211_{a-d}$ and catheter tip 205 are forwarded to signal conditioning circuitry 245 for one or more of the following: pre-amplification, analog-to-digital conversion, noise filtering, and signal isolation. Signal conditioning such as signal isolation and noise filtration are utilized to minimize error in later position determinations based on the received electrical signals. Analog-to-digital conversion is conducted when the processing circuitry 230 is a digital system. Signal conditioning, in many embodiments, is essential to minimize the resulting localization error rate of the magnetic distortion sensors and the catheter tip.

In preferred embodiments of the present disclosure, the signal conditioning circuitry 245 is coupled to the magnetic distortion sensor array to minimize attenuation of the noise when the received electrical signals are transmitted to processing circuitry 230. Also, amplification at this point is advantageous to increase the signal-gain prior to transmission to the processing circuitry.

Processing circuitry 230, as shown in FIG. 2, computes the perceived locations of magnetic distortion sensors $211_{a-d}$ and catheter tip 205, based on the electrical signal received from each of the magnetic distortion sensors and the catheter tip, the known/fixed location of each of the magnetic distortion sensors relative to the magnetic field transmitters 221 and a lookup table that associates sensed electric fields with a known position within the magnetic field. The known position may be a position with which there is relative certainty as to the position of the magnetic distortion sensors relative to the magnetic field transmitters coordinate system. In one exemplary embodiment, the processing circuitry 230 determines the discrepancy between an actual and perceived location for each of the magnetic distortion sensors $211_{a-d}$ by comparing a known/fixed position of the magnetic distortion sensor to a perceived position of the sensor. The perceived position is determined by sampling the electrical signal received by the magnetic distortion sensor and associating the sampled signal with a perceived location (via the look-up table). A discrepancy between the actual and perceived location of the magnetic distortion sensor is indicative of a magnetic distortion within the magnetic field. Once the discrepancy for each of the magnetic distortion sensors is determined, a transform is computed that corrects for the discrepancy between the perceived and actual location of each of the magnetic distortion sensors. The transform is then applied to the perceived location of the catheter tip 205 to determine the actual location of the catheter tip in view of the magnetic distortion(s) within the magnetic field.

Figure 3:
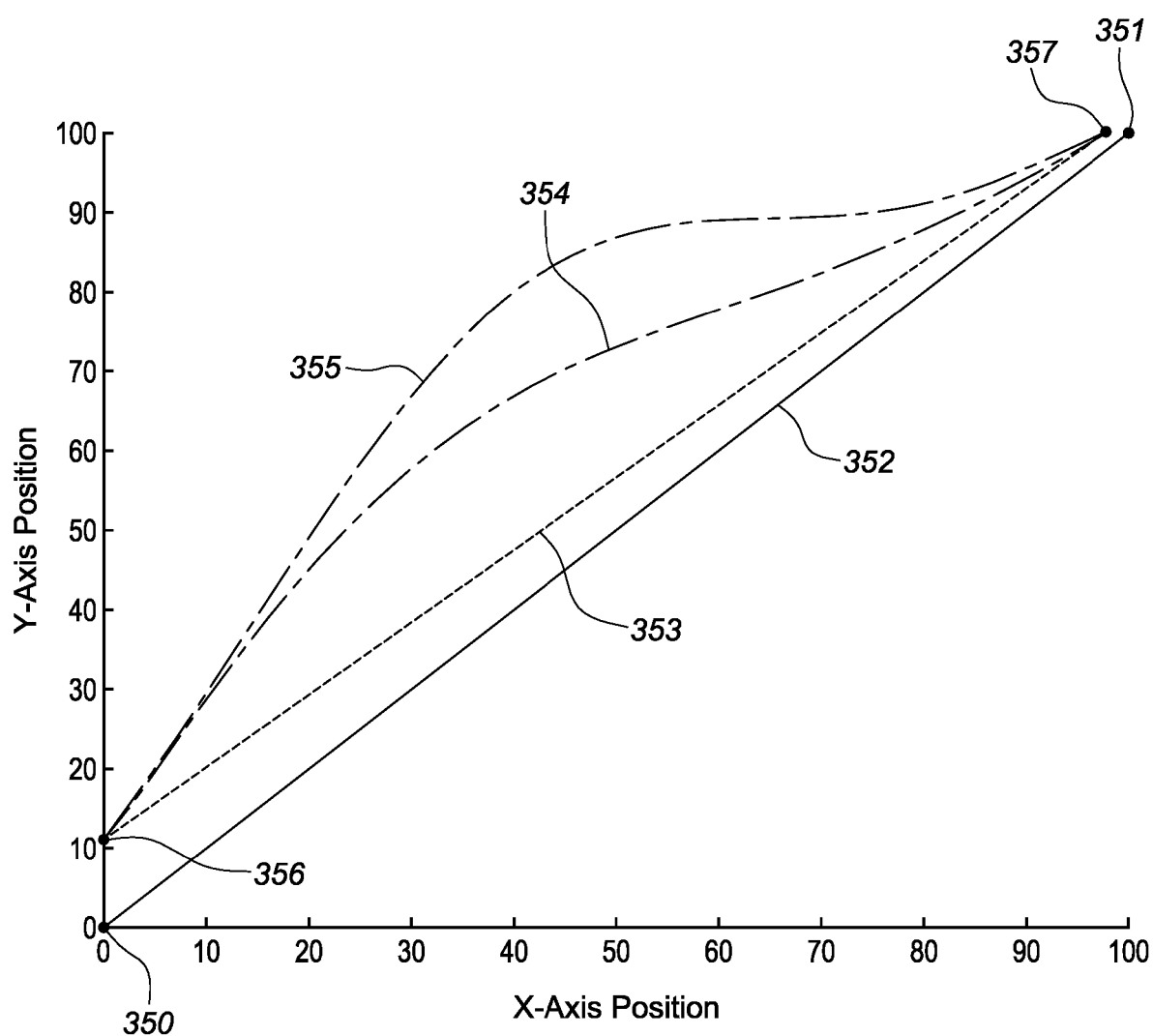
FIG. 3 is a graph showing the results of various methods of determining the effect of magnetic distortion (deformation) between known endpoints, consistent with various aspects of the present disclosure.

FIG. 3 is a graph showing experimental results consistent with aspects of the present disclosure. The graph shows the actual/fixed position of two sensor coils, the first sensor coil 350 at position (0, 0), and the second sensor coil 351 at position (100, 100); and a perceived location of the first sensor coil 356 at position (0, 10), and a perceived location of the second sensor coil 357 at position (95, 100). Various methodologies of fitting magnetic deformation to known/fixed endpoints are presented. Line 352 represents a fit between the first and second sensor coils that does not compensate for a sensed magnetic deformation within the two-dimensional coordinate system. Line 355 shows the actual underlying magnetic deformation. Line 353 shows a linear deformation calculation based only on the perceived and actual locations of the first and second sensor coils. Line 354 represents a non-linear deformation calculation (a Bezier spline fit) utilizing both the perceived and actual locations of the first and second sensor coils, as well as the slope there-between. By utilizing the slope between the locations of the first and second sensor coils, and use of spline fit allows for improved internal fitting of unknown deformation between fixed positions of the magnetic distortion sensor coils.

In certain specific embodiments, perceived locations of magnetic distortion sensor coils may be paired/grouped, such that an assessment of the gradient/slope of deformation can be determined at mid-points between the sensor coils. Various regression methods (as disclosed in more detail below) act as spline smoothers, for which the introduction of additional closely spaced points (via the pairings/groupings) on the exterior improve the interpolation accuracy on the interior. Such pairing/grouping may be accomplished by setting the position at the set of known/fixed magnetic distortion sensor coils, while the closely spaced pairings/groupings set the slope/gradient; this combination allows for the transformation to be "steered" into the area of the magnetic field including the anatomy of the patient being operated on. As a result, the interpolation of an actual position of a catheter within the patient's body is more accurate.

In another embodiment, a magnetic localization system may restore a location of a magnetic distortion sensor coil to the perceived location from a given point in time rather than from a known/fixed location. For example, the system could determine the perceived location of the magnetic distortion sensor coil at time t0. For future times, tn, the system would calculate a transform based on the discrepancy between each of the magnetic distortion sensor coils perceived locations at a time t0 and tn. Such an embodiment would allow for stabilization of the magnetic localization system's coordinate system over the course of a medical procedure thereby reducing or eliminating magnetic drifts (over time) that may be caused by the motion of a C-arm fluoroscopy system, or other intervening metal object(s) into the emitted magnetic field of the system.

Figure 4:
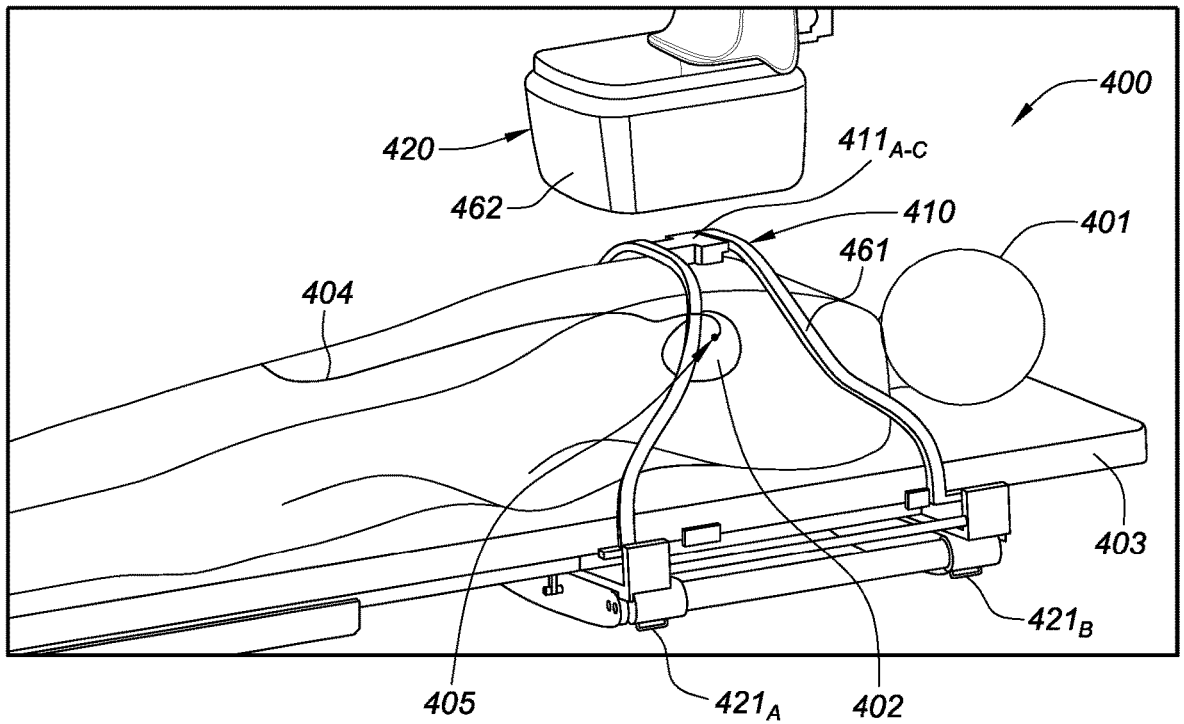
FIG. 4 is an isometric view of a magnetic distortion detection and correction system, consistent with various aspects of the present disclosure.

FIG. 4 shows an isometric view of a magnetic localization system 400 used for navigating the human anatomy of a patient 401 (located on an operating table 403) while conducting a medical procedure. For example, the system may be used to map a heart 402 of the patient and to navigate a cardiac catheter 404 through the chambers of the heart. Magnetic localization system 400 can determine the location and orientation of objects such as the tip 405 of the cardiac catheter 404. Specifically, the magnetic localization system 400 can be used to determine the location of the tip 405 of the cardiac catheter 404 within a magnetic field, which can then be overlaid onto, for example, an image or a model of the heart 402. The image of the heart may be collected, for example, from a fluoroscopy system 420 including a paired X-ray emitter and receiver 462. The X-ray receiver 462 is shown in FIG. 4 above the patient. The corresponding X-ray transmitter would be located opposite the X-ray receiver 462, below the patient 401.

Magnetic localization system 400 includes a plurality of magnetic field transmitters, with example magnetic field transmitters $421_{A-B}$ mounted below the operating table 403. In yet other embodiments, additional magnetic field transmitters may be utilized to expand the area of the magnetic field. In one specific example, four magnetic field transmitters 421 can be deployed in a square configuration, where the center of the square is positioned at an area of the patient where magnetic localization is to be conducted.

Each magnetic field transmitter 421 emits a magnetic field across a patient's body 401, and is powered by a magnetic field generator. The magnetic field generator generates one or more magnetic fields which may be transmitted by the magnetic field transmitters simultaneously, time multiplexed, and/or frequency multiplexed. Absent any magnetic distortion, each location within the magnetic field is associated with a unique magnetic field signature including a field gradient and strength. When a coil at a tip 405 of the medical device 404 senses the magnetic field in its proximity, the sensed relative magnetic field can be post-processed to determine a location of the tip 405 and its orientation.

For a cardiac ablation procedure, by way of example, a sensor coil array 410 is positioned directly above the patient's heart 402, opposite the plurality of magnetic field transmitters 421, and within the magnetic field emitted from the magnetic field transmitters 421. In the present embodiment, the sensor coil array 410 is affixed to and above the operating table 403 via supports 461, providing a fixed (and known) location of each magnetic distortion sensor coil 411$_{A-C}$ relative to the magnetic field transmitters 421. Each of the magnetic distortion sensor coils 411$_{A-C}$ sense the magnetic field, proximate to, and substantially co-planar with an orientation of the sensor coil in the sensor coil array 410, and output an electrical signal indicative of the sensed magnetic field at its fixed location. The outputted electrical signal of the magnetic distortion sensor coil is indicative of the perceived location of the sensor coil within the magnetic field. However, magnetic distortions within the magnetic field may cause a discrepancy between the actual location of a sensor coil in the fixed sensor coil array and a perceived location of the sensor coil by the magnetic localization system 400.

The tip of the catheter 405 includes one or more sensor coils that sense the magnetic field, proximate to, and substantially co-planar with the orientation of the sensor coil. Each of the catheter sensor coils outputs an electrical signal indicative of the sensed magnetic field at its location; which is unique to the specific location of the catheter within the magnetic field.

Outputs of magnetic distortion sensor coils 411$_{A-C}$ and sensor coils in the catheter tip 405 are transmitted to and sampled by processing circuitry. The processing circuitry performs computations based on the outputs of the sensor coils to determine, for example, the perceived location of a cardiac catheter within the heart.

To compensate for magnetic distortion in the magnetic localization system 400, sensor coil array 410 provides a fixed reference frame. The frame may include non-ferrous materials, or include such trace amounts of ferrous material as to have a limited/known effect on the magnetic field. Based on the discrepancy between the actual position and the perceived location of each of the magnetic distortion sensors 411$_{A-C}$ in the sensor coil array, the effect of the magnetic distortion throughout the magnetic field may be calculated and represented by a transform that restores the distorted-perceived locations of each of the magnetic distortion sensors back to the respective actual locations. Similarly, this transform may be applied to the distorted-perceived location of the catheter tip 405 within the magnetic field to determine a corrected (actual) location of the catheter 404 sans magnetic distortion.

In embodiments such as that presented in FIG. 4, the sensor coil array 410 is roughly centered about the patient's heart 402, which is receiving treatment by way of catheter tip 405. The sensor coil array 410 is desirably positioned in close proximity to the patient's heart, so that magnetic distortions affecting the catheter tip 405 are sensed by one or more of magnetic distortion sensors 411$_{A-C}$ in the sensor coil array 410.

To prevent inaccuracies in a magnetic localization system 400, magnetic localization system 400 utilizes one or more magnetic distortion sensors 411$_{A-C}$ to determine a discrepancy between actual locations (based on the known/fixed position of the magnetic distortion sensor within the system) and perceived locations (those determined based on the received magnetic fields at the magnetic distortion sensor and post-processing). The determined discrepancy is indicative of magnetic distortion throughout the magnetic field due to egress of ferrous/metallic objects into the magnetic field. Based on the discrepancy at each of the magnetic distortion sensor locations, a transform may be computed to correct for the distortion at all locations within the magnetic field. In such a system, magnetic distortions can be identified and corrected for in reference to the perceived location of catheter tip 405. Specific algorithms for determining and correcting for the existence of magnetic distortions within the magnetic field are presented below.

Figure 5:
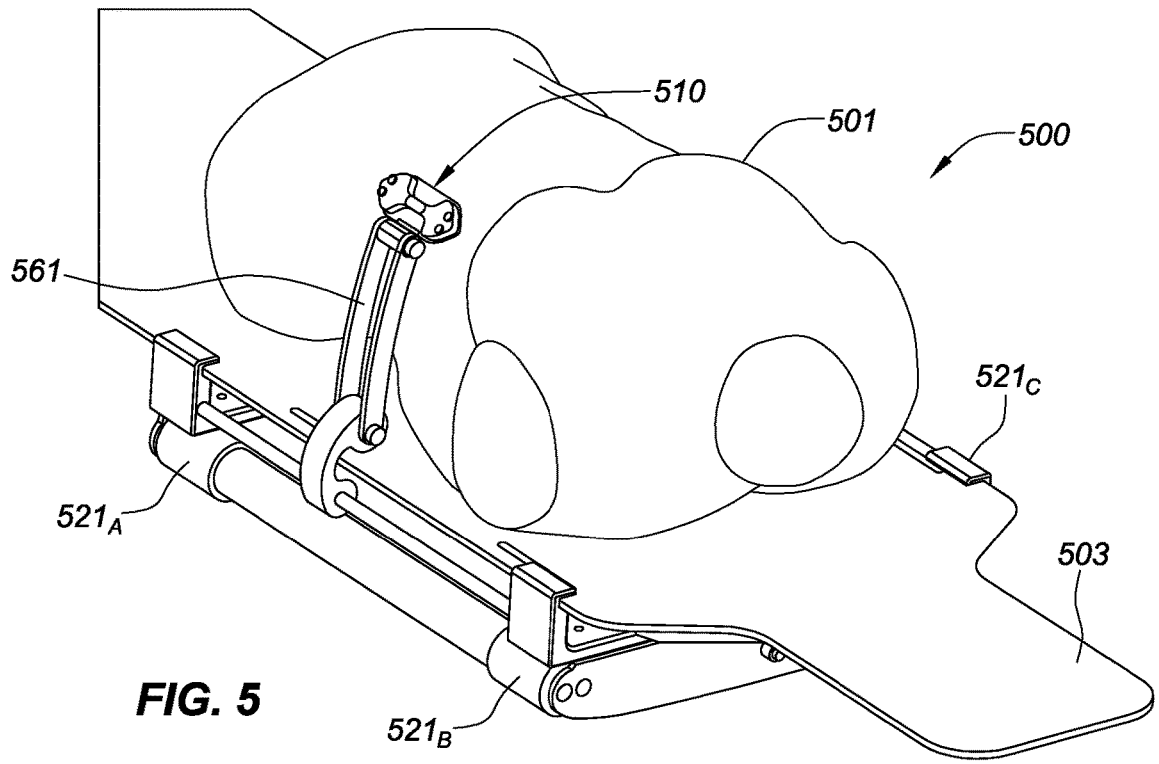
FIG. 5 is an isometric view of a magnetic distortion detection and correction system, consistent with various aspects of the present disclosure.

FIG. 5 is an isometric view of a magnetic distortion detection and correction system 500. A patient 501 is positioned on an operating room table 503 above magnetic field transmitters 521$_{A-D}$. The magnetic field transmitter 521$_D$ (not shown) is located opposite magnetic field transmitter 521$_A$, relative to the operating table 503. Once the patient 501 is stable on the operating table 503, sensor coil array 510 may be positioned at a location in proximity to an area of the patient being operated on, and within the magnetic field created by the magnetic field transmitters 521$_{A-D}$ via adjustable arm 561. A few particular benefits of the embodiment of FIG. 5 is a reduced foot-print that allows for easier clinician access to the patient, reduced de/installation time, and increased adjustability without the need to physically move the patient on the operating table 503. Also, as the sensor coil array 510 is laterally offset from the target area of the patient (e.g., the heart), the sensor coil array will not interfere with fluoroscopy imaging.

In various embodiments, adjustable arm 561 may include rotating elements, slider elements, among other adjustment facilitating elements. For example, as shown in FIG. 5, the adjustable arm 561 may be longitudinally adjusted (relative to the height of a patient 501) by sliding the adjustable arm along a track mounted parallel to a side of the operating table. To facilitate lateral adjustment and the angle of sensor coil array 510 relative to a target area of the patient 501, the adjustable arm can include a number of pivot points. The adjustable aspects of the arm help to facilitate precise location of the sensor coil array in close proximity to a target area where magnetic localization is to be conducted, while also accommodating patients of various sizes. In more specific embodiments, the adjustable arm 561 and related assembly may also include adjustment limits that prevent accidental positioning of the sensor coil array 510 outside of the magnetic field emitted by magnetic field transmitters 521$_{A-D}$, where the sensor coil array would be ineffective at detecting magnetic distortion.

In various embodiments consistent with FIG. 5, the magnetic distortion detection and correction system 500 may include two or more sensor coil arrays 510 positioned (via adjustable arms 561) in proximity to an area of the patient being operated on, and within the magnetic field created by the magnetic field transmitters 521$_{A-D}$. The various sensor coil arrays 510 may be longitudinally and laterally offset from one another (relative to the patient). Accordingly, various embodiments consistent with the present disclosure may include one or more sensor coil arrays mounted on a same side of the patient, and/or one or more sensor coil arrays mounted on opposite sides of the patient. In various embodiments, these multiple sensor coil arrays are positioned in proximity to a target area of the patient for magnetic localization. By positioning the plurality of sensor coil arrays in such a manner as to essentially surround the target area, the sensor coil arrays can detect and correct for magnetic distortions emanating from various ferrous objects in proximity to the magnetic field and target area.

As shown in the embodiments of FIGS. 4 and 5, the magnetic distortion sensors are configured in a single fixed location. The algorithms disclosed in more detail below can accomplish translation and rotation correction with such a single fixed location; however, warping correction may require additional magnetic distortion sensors if the warping correction is to minimize extrapolation. Accordingly, various embodiments of the present disclosure may include two or more magnetic distortion sensors to minimize extrapolation for the warping correction.

In various specific/experimental embodiments of the present disclosure, a magnetic localization system may utilize visually tracked fiducials (placed in a field of view of an imaging system) to provide a point of reference that may be used to merge a location of a medical device detected by the localization system, in a first coordinate frame with a produced image from the imaging system (e.g., fluoroscopy, other X-ray type imaging, etc.) in a second coordinate frame.

Figure 6:
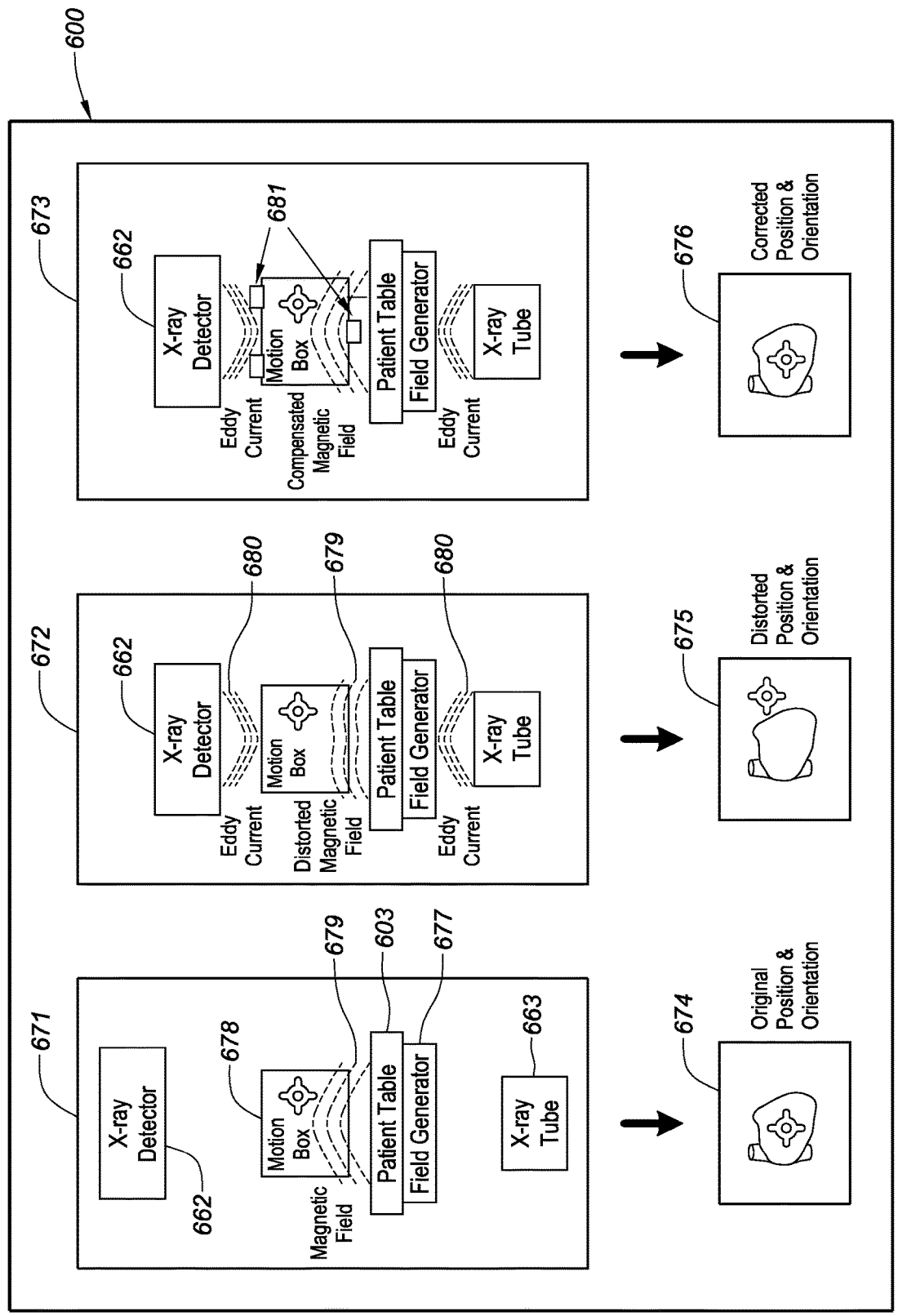
FIG. 6 is a diagram of various operating room suite configurations including a medical device localization system and exemplary localization results for each configuration, consistent with various aspects of the present disclosure.

FIG. 6 is a diagram 600 of various operating room suite configurations including a medical device localization system and exemplary localization results for each configuration. Suite configuration 671 shows X-ray detector 662 and X-ray tube 663 located at nominal positions, where the magnetic components of the X-ray detector and X-ray tube are located far enough from a magnetic field 679 emitted from magnetic field transmitter 677 (through patient table 603) so as not to distort the magnetic field. As a result, the localization of an object within motion box 678 (an area within which localization of the medical device can take place) is accurate, as shown in an exemplary display image 674 showing the appropriate position of the object, within the patient's cardiac muscle.

Suite configuration 672 shows X-ray detector 662 and X-ray tube 663 located at undesirable positions, where the magnetic components of the X-ray detector and X-ray tube are located within a magnetic field 679 emitted from magnetic field transmitter 677 (also referred to as a field generator), distorting the magnetic field around motion box 678 via eddy currents 680. As a result, the localization of an object within the motion box 678 is inaccurate. As shown in exemplary display image 675, even though the localized object is within the patient's cardiac muscle, the magnetic distortion from the magnetic components within the magnetic field causes the false localization of the object outside of the cardiac muscle.

Suite configuration 673 shows X-ray detector 662 and X-ray tube 663 located at undesirable positions, where the magnetic components of the X-ray detector and X-ray tube are located within a magnetic field 679 emitted from magnetic field transmitter 677, distorting the magnetic field around motion box 678 via eddy currents 680. As a result, the localization of an object within the motion box 678 is inaccurate. Each of the magnetic distortion sensors 681 placed around the outer periphery of the motion box 678 detect whether the magnetic field at its known location is distorted. In response to the distortion, a transform can be calculated based on the data provided by the magnetic distortion sensors and applied to the object within the motion box. As shown in exemplary display image 676, even though the localized object is located within a distorted magnetic field, the transform corrects the perceived location of the object and correctly positions it within patient's cardiac muscle.

Figure 7A:
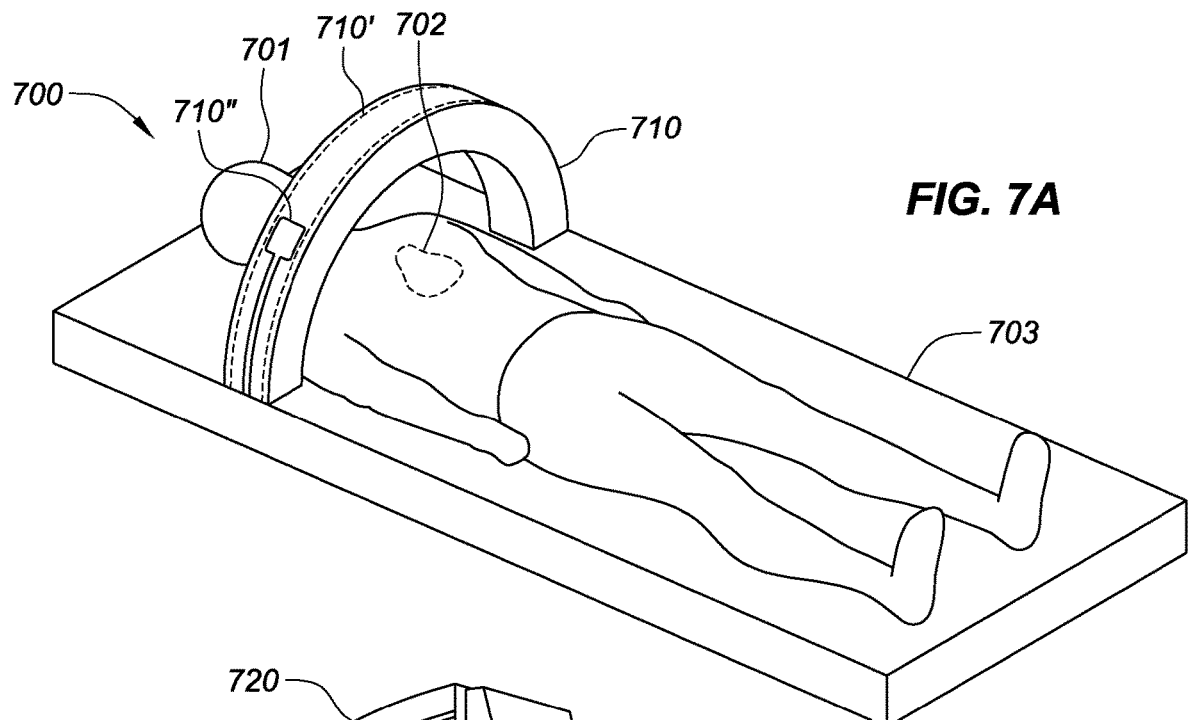
FIG. 7A is an isometric view of a magnetic distortion detection and correction system, consistent with various aspects of the present disclosure.

FIG. 7A shows an isometric view of a magnetic localization system 700 used for navigating the human anatomy of a patient 701 while conducting a medical procedure. For example, the system may be used to map a heart 702 of the patient and to navigate a cardiac catheter 705 through the chambers of the heart. Magnetic localization system 700 determines the location (and, in some embodiments, the orientation) of objects (e.g., a portion of a diagnostic or ablation catheter, such as the tip of the cardiac catheter), typically within a three dimensional space, and expresses those locations as position information determined relative to at least one reference. Specifically, the magnetic localization system 700 can be used to determine the location of the cardiac catheter 705 within a magnetic field, which is then overlaid onto, for example, an image or a model of the heart 702. In more specific embodiments, magnetic resonance imaging data, among other reference data, may be overlaid onto the three-dimensional space to provide a clinician with a virtual work environment in which to reference for real-time position of the cardiac catheter relative to the patient's heart.

The magnetic localization system 700 may include various visualization, mapping, and navigation components. For example, the localization system 700 may include a magnetic-field-based system such as the CARTO™ system commercially available from Biosense Webster, the MEDI-GUIDE™ Technology system available from St. Jude Medical, Inc., a hybrid electric-field-based and magnetic-field-based system, or the CARTO™ 3 system commercially available from Biosense Webster. In yet other exemplary embodiments, the localization system 700 may comprise, or be used in conjunction with, other commonly available imaging systems, such as, for example and without limitation, fluoroscopic, computed tomography (CT), and magnetic resonance imaging (MRI)-based systems.

Figure 7B:
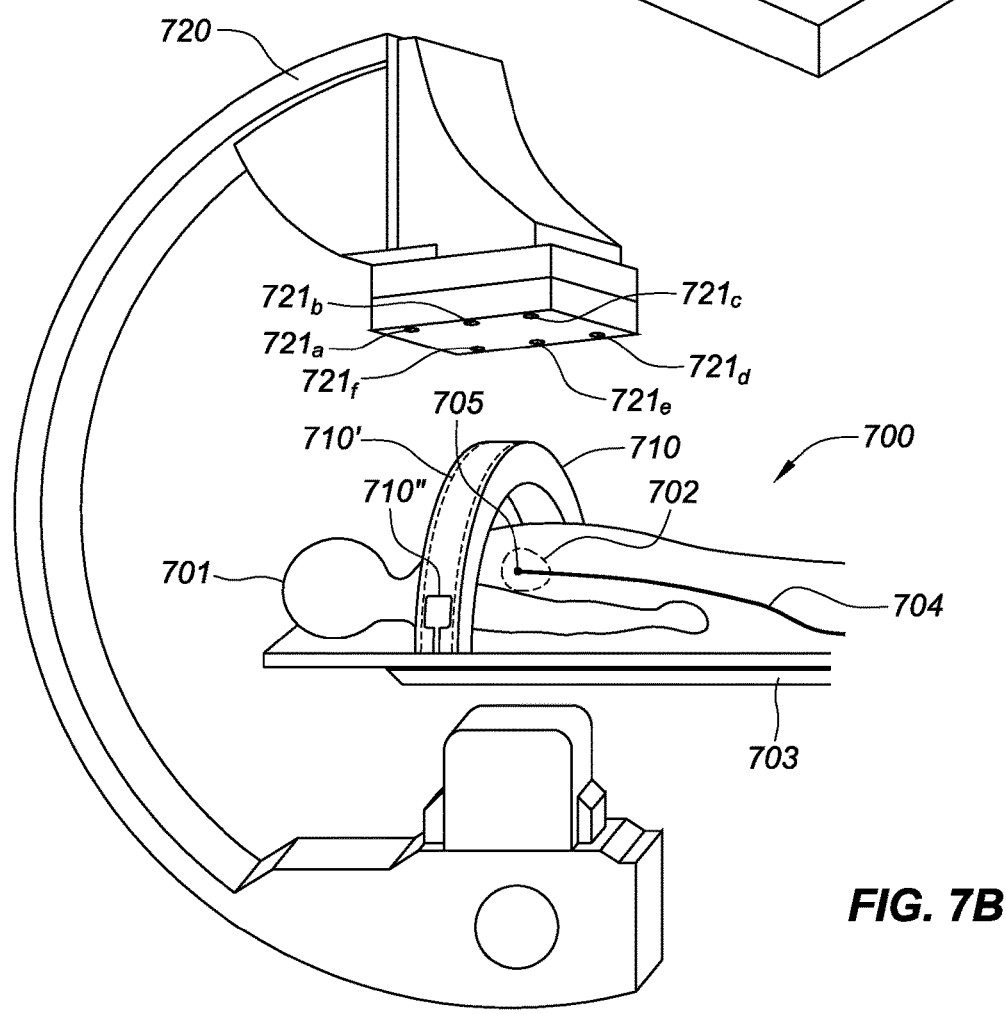
FIG. 7B is a side-view of the magnetic distortion detection and correction system of FIG. 7A with a C-arm for fluoroscopic imaging and magnetic field emission, consistent with various aspects of the present disclosure.

A single-use catheter assembly 704, as shown in FIG. 7B, may include a catheter tip assembly 705 (also referred to as an electrode assembly or distal tip assembly) at a distal end. The catheter tip assembly may be operatively adapted for conducting a diagnostic or therapeutic procedure under clinician control. The catheter tip assembly may perform, for example, localization, mapping, ablation, and/or pacing procedures. To facilitate localization, the catheter tip assembly may include a plurality of localization sensor coils (e.g., magnetic field sensors).

As shown in FIG. 7B, a magnetic localization system 700 includes a plurality of magnetic field transmitters $721_{a-f}$ in a magnetic field transmitter housing 720. In various embodiments of the present disclosure, the magnetic field transmitters may be incorporated into a fluoroscopy imaging system (referred herein as the magnetic field transmitter housing 720), such as a C-Arm. Each of the magnetic field transmitters emit a magnetic field across a patient's body 701. Absent a magnetic distortion, each location within the magnetic field is associated with a unique magnetic field signature (including, for example, a unique field gradient and strength).

During an intracardiac procedure, by way of example, a shuttle housing 710 is positioned at least partially circumferential to the patient's heart 702. The shuttle housing 710 may in some embodiments be positioned between the magnetic field transmitter housing 720 (within the magnetic field emitted therefrom) and one or more magnetic sensors within a distal tip 705 of the catheter 704. In the present embodiment, the shuttle housing 710 is affixed to operating table 703, providing a known location of a shuttle track 710' within the shuttle housing 710. The shuttle track 710', in FIGS. 7A-B, is a lumen that extends through the shuttle housing 710. A shuttle 710" may be extended through the shuttle track 710', and thereby follow an arc over the patient 701. As the shuttle 710" is drawn through the shuttle track 710', the exact position of the shuttle 710" is associated with a magnetic field strength and gradient measured by one or more magnetic distortion sensor coils on or within the shuttle 710". In some specific embodiments, each of the magnetic distortion sensor coils on the shuttle 710" sense the magnetic field, proximate to, and substantially co-planar with an orientation of the sensor coil in the sensor coil array, and outputs an electrical signal indicative of the sensed magnetic field at the known location of the shuttle 710" at a particular instance in time. The electrical signal output of the magnetic distortion sensor coils are indicative of the perceived location of the sensor coils within the magnetic field; however, magnetic distortions within the magnetic field may cause a discrepancy between the known location of the sensor coils within the shuttle housing 710, and the perceived location of the sensor coils by the magnetic localization system 700.

Output signals from the magnetic distortion sensor coils $711_{a-f}$ and magnetic sensors within a distal tip 705 of the catheter 704 are transmitted to and sampled by processing circuitry. The processing circuitry performs computations based on the outputs of the sensor coils to determine, for example, the perceived location of a cardiac catheter within the heart. The perceived location of the cardiac catheter may be used for reference by a clinician during a procedure, and be presented to the clinician on a display in relation to known reference points, e.g., cardiac chambers, arteries, etc. However, the actual catheter position may be obscured by magnetic distortions within the magnetic field caused by other ferrous/metallic bodies in proximity to the magnetic localization system 700. These magnetic distortions are associated with an error rate of the perceived position of the catheter compared to the actual position of the catheter.

To compensate for magnetic distortion in the magnetic localization system 700, the shuttle housing 710 in combination with the shuttle 710" provides a known reference frame, and may define the origin of the system's coordinate frame. Based on the discrepancy between the actual position and the perceived location of each of the magnetic distortion sensors within the shuttle 710", the effect of the magnetic distortion throughout the magnetic field may be calculated and represented by a transform that restores the perceived locations of each of the magnetic distortion sensor coils of the shuttle 710" back to the respective actual locations. Similarly, this transform may be applied to the perceived location of a distal tip 705 of the catheter 704 within the magnetic field to determine a corrected (actual) location of the catheter tip in view of the magnetic distortion.

Catheter 704 may include one or more magnetic sensors coils in its tip region 705 which sense the magnetic field strength and gradient proximate the catheter tip region. As discussed above, the sensed magnetic field at the location of the catheter tip 705 within the magnetic field is unique to that location within the magnetic field. Based on the sensed magnetic field at the tip of the catheter, processing circuitry may determine, where the coil is located in the magnetic field and correct for magnetic distortion within the magnetic field. This information, in conjunction with other known locations within the coordinate system (e.g., chambers, valves, and arteries) allows a clinician to navigate the catheter within the patient's heart using the (near) real-time position data provided by the magnetic localization system 700.

Figure 8A:
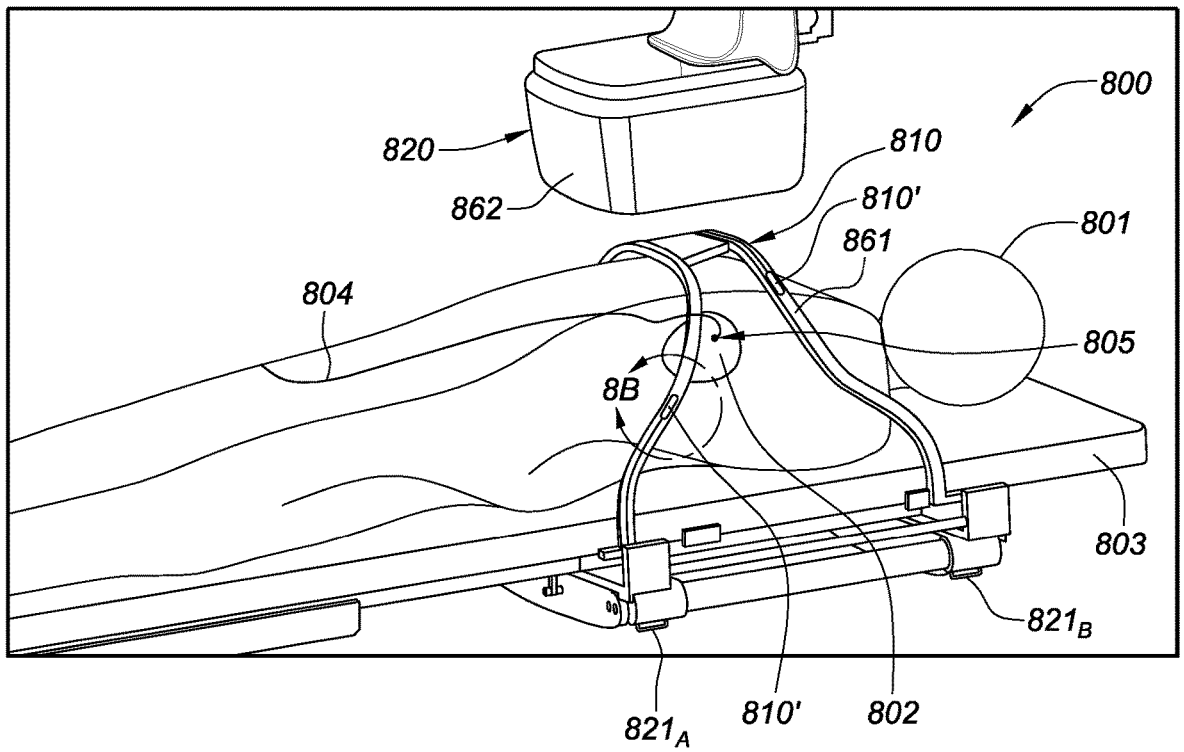
FIG. 8A is an isometric view of a magnetic distortion detection and correction system, consistent with various aspects of the present disclosure.

FIG. 8A shows an isometric view of a magnetic localization system 800 used for navigating the anatomy of a patient 801 (located on an operating table 803) while conducting a medical procedure. For example, the system may be used to map a heart 802 of the patient and to navigate a cardiac catheter 804 through the chambers of the heart. Magnetic localization system 800 can determine the location and orientation of objects such as the tip 805 of the cardiac catheter 804. Specifically, the magnetic localization system 800 can be used to determine the location of the tip 805 of the cardiac catheter 804 within a magnetic field, which can then be overlaid onto, for example, an image or a model of the heart 802. The image of the heart may be collected, for example, from a fluoroscopy system 820 including a paired X-ray emitter and receiver 862. The X-ray receiver 862 is shown in FIG. 8A above the patient. The corresponding X-ray transmitter would be located opposite the X-ray receiver 862, below the patient 801.

Magnetic localization system 800 includes a plurality of magnetic field transmitters, with example magnetic field transmitters $821_{A-B}$ mounted below the operating table 803. In yet other embodiments, additional magnetic field transmitters may be utilized to expand the area of the magnetic field. In one specific example, four magnetic field transmitters $821_{A-B}$ can be deployed in a square configuration, where the center of the square is positioned at an area of the patient where magnetic localization is to be conducted. When a coil at a distal tip 805 of the catheter 804 senses the magnetic field in its proximity, the sensed relative magnetic field can be post-processed by controller circuitry to determine a location of the tip 805 and its orientation.

For a cardiac ablation procedure, by way of example, one or more shuttle housings 810 may be positioned in proximity to the patient's heart 802, opposite the plurality of magnetic field transmitters $821_{A-B}$, and within the magnetic field emitted from the magnetic field transmitters 821. In the present embodiment, the shuttle housing 810 is affixed to and above the operating table 803 via supports 861, providing a known location of each shuttle 810' relative to the magnetic field transmitters 821 via shuttle tracks 810". Each of the one or more shuttles 810' may be manipulated along respective shuttle tracks 810", each of the shuttles 810' may include one or more magnetic distortion sensor coils which sense the magnetic field at the known location of the shuttle 810', and output an electrical signal indicative of the sensed magnetic field at the known location of the shuttle 810'. The shuttle 810' may be manipulated along a shuttle track 810", with a known location which processing circuitry associates with the magnetic field sensed at that location. The electrical signal output by the magnetic distortion sensor coil is indicative of the perceived location of the sensor coil within the magnetic field at that instance in time. However, magnetic distortions within the magnetic field may cause a discrepancy between the known location of a sensor coil and a perceived location of the sensor coil by the magnetic localization system 800.

Signals from the magnetic distortion sensor coils within shuttle 810' and sensor coils in the catheter tip 805 are transmitted to and sampled by processing circuitry. The processing circuitry performs computations based on the signals received from the sensor coils to determine, for example, the perceived location of a cardiac catheter within the heart.

To compensate for magnetic distortion in the magnetic localization system 800, shuttle 810' provides a known reference frame (as the position of the shuttle 810' on track 810" is known at all times). Based on the discrepancy between the known position and the perceived location of each of the magnetic distortion sensors in/on the one or more shuttles 810', the effect of the magnetic distortion throughout the magnetic field may be calculated and represented by a transform that restores the distorted-perceived locations of each of the magnetic distortion sensors back to the respective actual locations. The transform may then be applied to the distorted-perceived location of the catheter tip 805 within the magnetic field to determine a corrected (actual) location of the catheter tip 805 sans magnetic distortion.

Figure 8B:
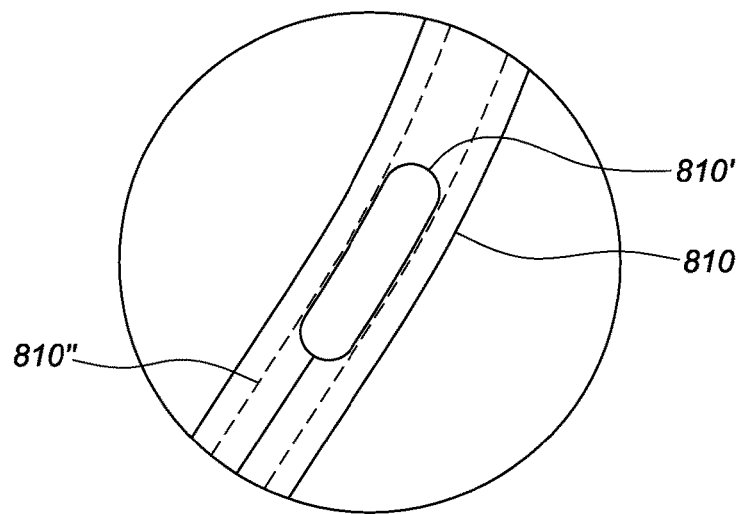
FIG. 8B is an expanded isometric view of the magnetic distortion detection and correction system of FIG. 8A.

FIG. 8B is an expanded isometric view of the magnetic distortion detection and correction system of FIG. 8A. A shuttle housing 810 includes one or more shuttle tracks 810" (e.g., a lumen) that extend a length of the shuttle housing 810. One or more shuttles 810' may be extended through the shuttle tracks 810" in such a way as to accurately sense a position of the shuttle 810' as it extends through the shuttle housing. In some specific embodiments, the shuttle may be drawn along the shuttle tracks 810" via a pull wire, pushed along the tracks, driven along the tracks, actuated, or otherwise moved in a precise manner. In several embodiments, only the distance the shuttle 810' has traveled along a track 810" must be known and a lookup table may associate the distance with a known position within a Cartesian coordinate system of a magnetic localization system.

Figure 9:
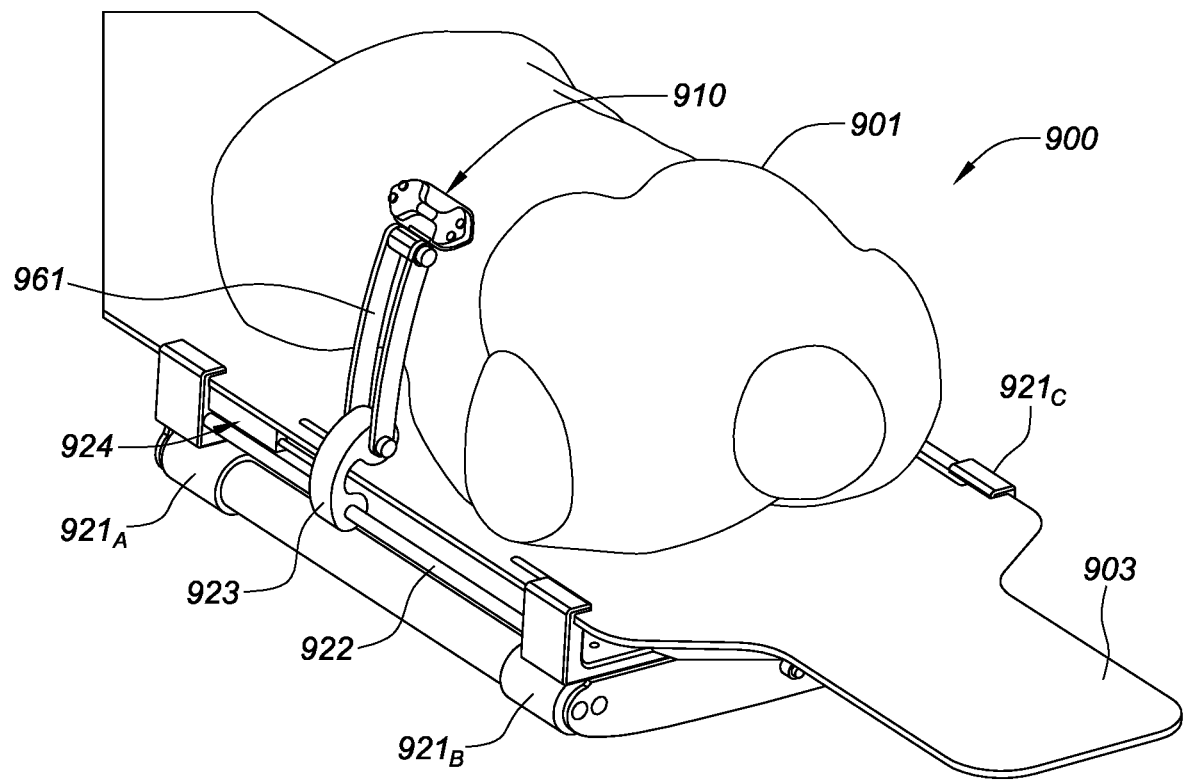
FIG. 9 is an isometric view of a magnetic distortion detection and correction system, consistent with various aspects of the present disclosure.

FIG. 9 is an isometric view of a magnetic distortion detection and correction system 900. A patient 901 is positioned on an operating room table 903 above magnetic field transmitters $921_{A-C}$. Once the patient 901 is properly positioned on the operating table 903, sensor coil array 910 may be positioned at a location in proximity to an area of the patient being operated on, and within the magnetic field created by the magnetic field transmitters $921_{A-C}$ via adjustable arm 961. A few particular benefits of the embodiment of FIG. 9 is a reduced foot-print that allows for easier clinician access to the patient, reduced de/installation time, and increased adjustability without the need to physically move the patient on the operating table 903. Also, as the sensor coil array 910 is laterally offset from the target area of the patient (e.g., the heart), the sensor coil array will not interfere with fluoroscopic imaging.

In various embodiments, adjustable arm 961 may include rotating elements, slider elements, among other adjustment facilitating elements. For example, as shown in FIG. 9, the adjustable arm 961 may be longitudinally adjusted (relative to the height of a patient 901) via an actuator 924 that slides the adjustable arm 961 along a track 922 mounted parallel to a side of operating table 903. To facilitate lateral adjustment, and an incidence angle of the sensor coil array 910, relative to a target area of the patient 901, the adjustable arm 961 may further include additional actuators therefore. To correct for magnetic distortions in proximity to the patient, that may otherwise impede the accuracy of the magnetic localization system, the sensor coil array 910 may be actuated longitudinally, laterally, and/or relative to an angle of incidence between the adjustable arm 961 and the patient 901. The known location of the sensor coil array 910 during its actuation and a sensed magnetic field at that location are then associated with one another in a look-up table, for example Magnetic fields at locations between sensed positions may be extrapolated. Based on the sensed magnetic fields across the actuation range of the sensor coil array 910, an error for each of the locations may be determined and a transform calculated to correct for the detected magnetic distortions. In some specific embodiments, the one or more actuators 924 may move the sensor coil array 910 via the adjustable arm 961 in a triangular or square pattern within a plane above the patient 901. In yet other embodiments, a three-dimensional path over the patient may provide for an improved error transform—for example, following edges of an imaginary cube above the patient 901.

As shown in the embodiments of FIGS. 8A-B and 9, the magnetic distortion sensors are configured to move along one or more paths with the location of the sensors being known throughout the movement and associated with a sensed magnetic field at that particular location. Due in part to the infinite number of data points that may be collected through such embodiments, extrapolation for the warping correction (also referred to as the transform) may be greatly minimized.

Figure 10A:
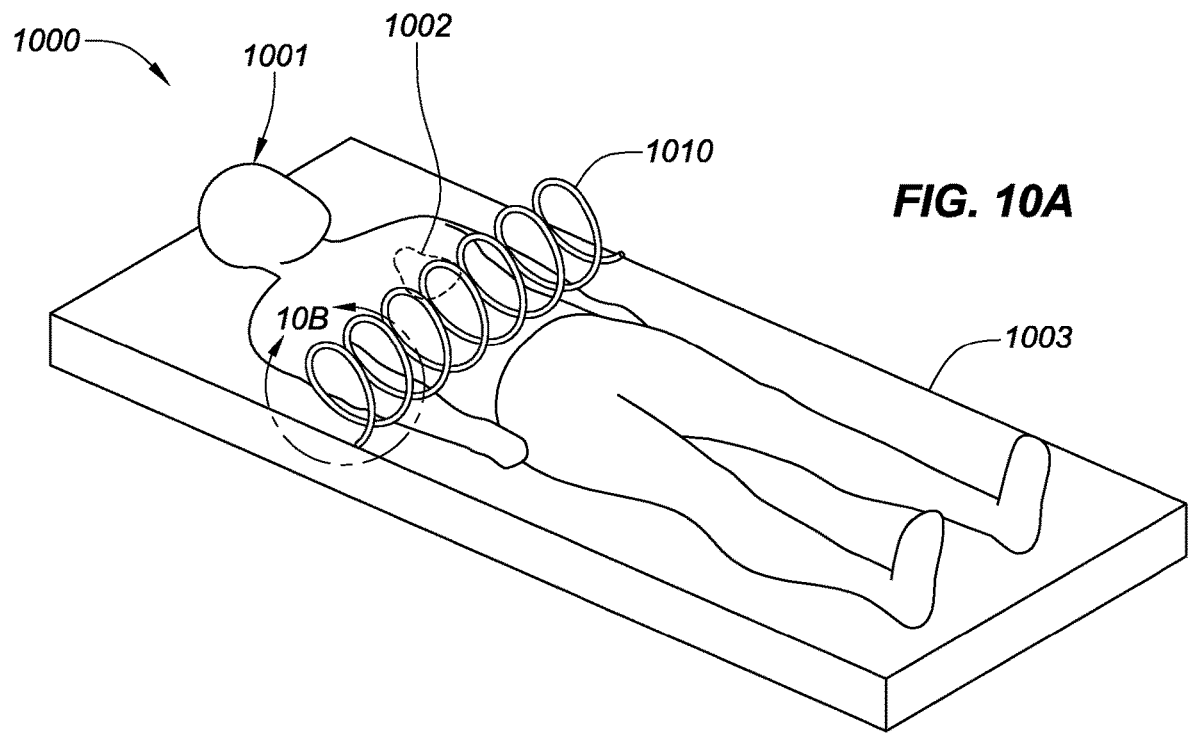
FIG. 10A is an isometric view of a magnetic distortion detection and correction system, consistent with various aspects of the present disclosure.

FIG. 10A is an isometric view of a magnetic distortion detection and correction system 1000, consistent with various aspects of the present disclosure. As shown in FIG. 10A, a shuttle housing 1010 helically extends over a target area 1002 (e.g., a cardiac muscle) of a patient 1001. The shuttle housing 1010 may be coupled to an operating table 1003, or otherwise positioned in such a way that the various locations of a shuttle within the shuttle housing 1010 is known relative to a coordinate system of a localization system. Accordingly, a magnetic field sensed by a shuttle within the shuttle housing 1010 may be associated with a known location of the shuttle and appended to a look-up table. The lookup table may then be used to determine a transform that corrects for the effect of a magnetic distortion within the magnetic field. By applying the transform to perceived locations of, for example, a catheter within the magnetic field, a corrected/actual location of the catheter may be determined.

Figure 10B:
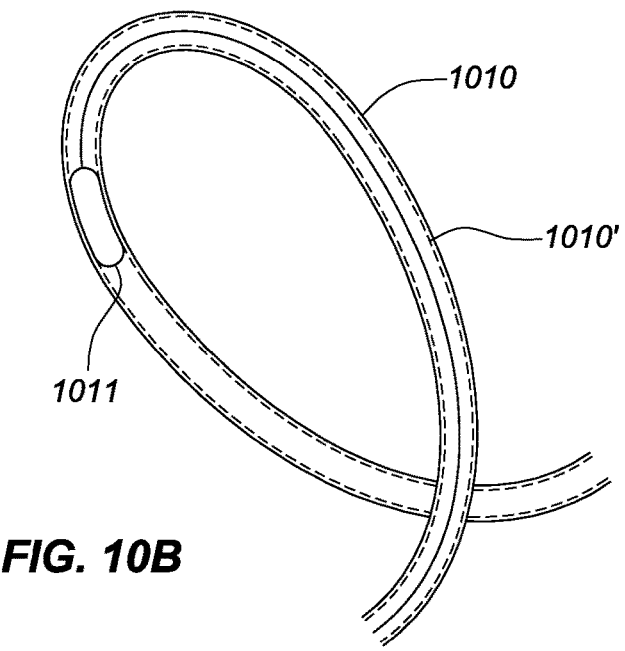
FIG. 10B is an expanded isometric view of the magnetic distortion detection and correction system of FIG. 10A.

FIG. 10B is an expanded isometric view of the magnetic distortion detection and correction system 1000 of FIG. 10A. The helically-shaped shuttle housing 1010 further includes a shuttle track 1010' that facilitates the travel of shuttle 1011 (including one or more magnetic sensors) through the shuttle housing 1010. An actuator may be used to precisely control the movement of the shuttle 1011 through the shuttle housing 1010—thereby allowing for the determination of a location of the shuttle 1011 relative to a coordinate system of the localization system. In more specific embodiments, the shuttle housing 1010 may comprise a helix following an arch extending over a target area of the patient 1001.

Figure 11:
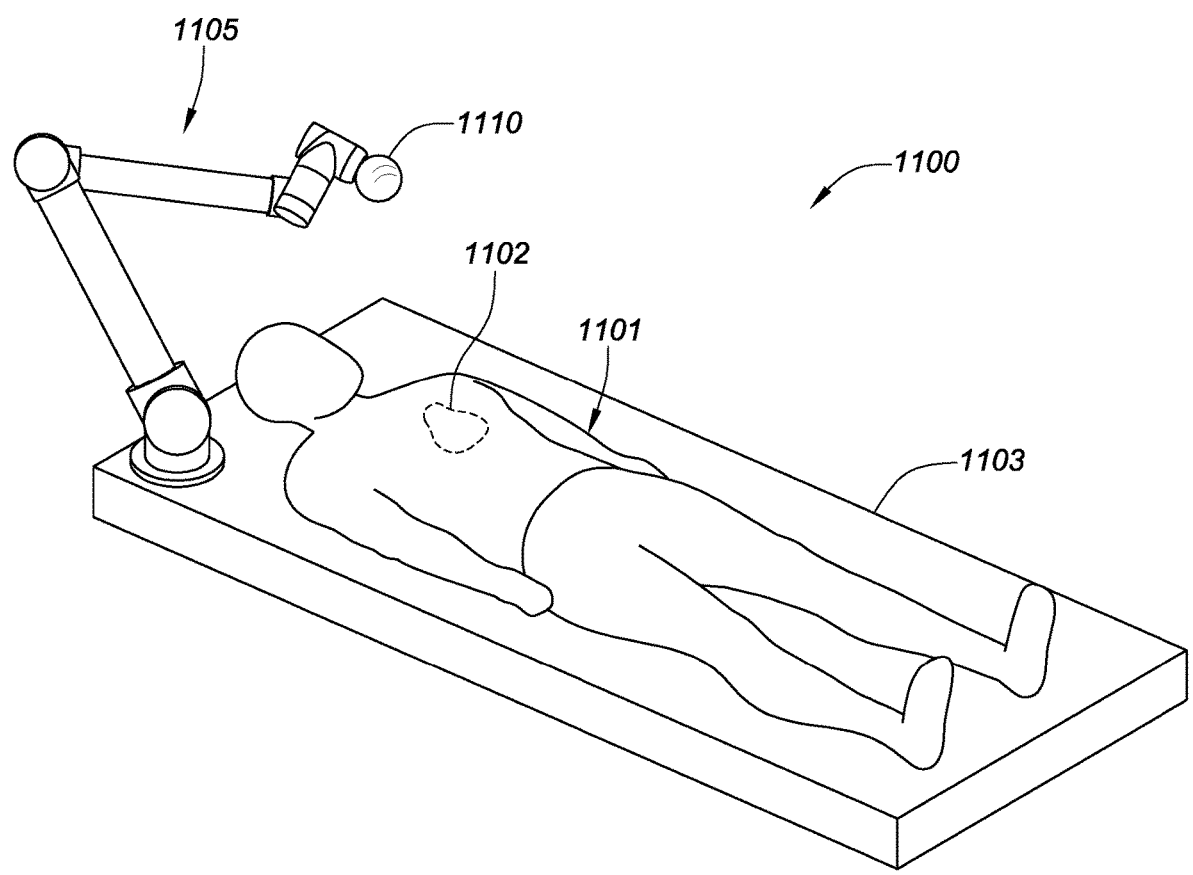
FIG. 11 is an isometric view of a magnetic distortion detection and correction system, consistent with various aspects of the present disclosure.

FIG. 11 is an isometric view of a magnetic distortion detection and correction system 1100, consistent with various aspects of the present disclosure. In FIG. 11, a patient 1101 is positioned on top of an operating table 1103. A target area 1102 (e.g., a cardiac muscle) of the patient 1101 is positioned in proximity to a robotic arm 1105. To check for magnetic distortions within a magnetic field that may impede the accuracy of a magnetic localization system used to determine a position of a medical device within a patient (for example), the robotic arm 1105 may be programmed to follow one or more pre-programmed paths. An end effector 1110 of the robotic arm 1105 may include one or more magnetic sensor coils that measure a strength and gradient of the magnetic field at the end effector 1110. Once the magnetic measurements at the various known locations of the robotic arm 1105 path have been taken, the magnetic measurements may be associated with the known locations of the measurements—thereby facilitating a transform calculation for correcting a field distortion within the magnetic field.

In more specific embodiments, the robotic arm 1110 may follow an exploratory path that varies based on a sensed magnetic field and a real-time calculation of localization accuracy at that location. For example, upon sensing a large magnetic distortion, the robotic arm 1110 may follow a path that facilitates further investigation of the area suffering from a large magnetic distortion. Further magnetic measurements in this area may facilitate an improved transform algorithm and a more accurate localization system. Similarly, in an area with a real-time localization accuracy within an acceptable threshold, the robotic arm 1110 may decrease the number of measurements taken in this area, and/or otherwise adjust the exploratory path to focus on areas where a large magnetic distortion has been detected.

In embodiments where the magnetic sensors are manipulated by an actuator and/or robotic arm consisting of conductive materials, a non-conductive extender may extend out from the actuator and/or robotic arm, with the magnetic sensor coupled to a distal tip thereof. Such a configuration would eliminate or at least greatly reduce the magnetic distortions to the magnetic field associated with the actuator and/or robotic arm. Alternatively, an actuator and/or robotic arm devoid of any conductive materials may be used.

Based on the specific/experimental magnetic distortion detection algorithms disclosed below, one of skill in the art is readily capable of deriving numerous other detection and correction algorithms.

Specific/Experimental Magnetic Distortion Correction Algorithms

One way to correct for magnetic distortion is to use a registration transformation that allows for local warping. In effect such a transformation incorporates bending which forces an exact correspondence at the fiducial points (known/fixed positions of the magnetic distortion sensor coils). Therefore the following mapping is desired:

$$f: \Re^3 \to \Re^3 \quad (1)$$

such that for each of the fiducial point pair $s_i = (x_i, y_i)$, the error defined as:

$$e_i = |f(x_i) - y_i| \quad (2)$$

is driven to zero (0) for each fiducial point.

Additional constraints are desirable to ensure that the magnetic distortion mapping is continuous and smooth in between the fiducial points. In the case where there is knowledge that the fiducial pairs may incorporate some misidentification error, the mapping may also include increased regularization to smooth the transform (so as not to over-fit the data).

Registration methods that determine mapping, f, include, for example: Thin Plate Splines; Mean Value Coordinates; and Radial Basis Function Networks. Each of these methods are described in more detail below.

Thin Plate Splines

Thin Plate Splines (TPS) is a method of interpolation between a set of fiducials. TPS may be applied where the set of control points are needed to determine a surface in three-dimensional space, where (x,y) are the input values and z is the output value. In our case we need to determine a set of surfaces in four-dimensional space where vector x is the input value and vector y is the output value. The TPS solution is the sum of a set of weighted basis functions centered at each control point, where the basis function is typically:

$$r^2 \log r, \text{ for the case of } f: \Re^2 \to \Re^1 \quad (3)$$

and $$r, \text{ for the case of } f: \Re^3 \to \Re^3 \quad (3)$$

where r is the radial distance of an input point from the particular basis function center.

The number of basis functions is equal to the number of control points and the weights for each basis function are determined through solving a set of linear algebraic equations. A regularization parameter, $\overline{k}$, can be introduced into this calculation to smooth the solution.

Thin Plate Spline methodologies are further disclosed in Bookstein, F. L., Principal Warps: Thin Plate Splines and the Decomposition of Deformations, IEEE Trans. Pattern Anal. Mach. Intell. 11, 567-585, 1989, which is hereby incorporated by reference in its entirety as though fully set forth herein.

Mean Value Coordinates

Mean Value Coordinates (MVC) is an algorithm that transforms individual points in three-dimensions relative to a "control mesh"—a closed, triangulated surface in three-dimensions. When this mesh is deformed, the algorithm can compute a smooth interpolation function throughout the three-dimensional space that (exactly) deforms the vertices and triangles and does not wildly extrapolate in regions far from the mesh. The fiducial pair of (x,y,z) coordinates comprise the vertices of the control mesh, which deforms the coordinates of the localization system to a coordinate system more accurately representing the actual physical coordinate system. The vertices are connected by a projection of the vertices onto a sphere centered at a cumulative centroid and computing its convex hull (via a two-dimensional Delaunay triangulation). The Mean Value algorithm then uses the control and deformed meshes to efficiently and smoothly transform any coordinate from one coordinate space to another space. Its operation count is linearly proportional to the number of vertices and triangles in the control mesh. With a sufficient number and quality of fiducial points, Mean Value Coordinates can account for both global rotation and scaling differences between two coordinate spaces as well as the local warping due to inhomogeneities.

MVC methodologies are further disclosed in Ju T, Schaefer S, Warren J, Mean value coordinates for closed triangular meshes, ACM Transactions on Graphics, July 2005, 24(3):561-566, which is hereby incorporated by reference in its entirety as though fully set forth herein.

Radial Basis Function Networks

Radial Basis Function networks (RBFN) are a method for performing function regression through the summation of a network of basis (or kernel) functions centered in various locations. In one exemplary RBFN:

$$y = f(x) \equiv \sum_{i=0}^{I} h_i \kappa((x - c_i)/w_i) \quad (4)$$

where κ is the basis function, which is typically of Gaussian shape:

$$\kappa(x) = \frac{1}{\sigma\sqrt{2\pi}} e^{-(x-\mu)^2/2\sigma^2},$$

$h_i$ is the height or weighting for each basis function; $w_i$ is the width of the basis function; and $c_i$ is the center of the basis function. Each of these parameters must be determined from the samples provided. There are various methods for learning these parameters from a set of samples. One common method is to use techniques motivated by neural networks, such as gradient descent.

The methodologies as presented above are further disclosed in U.S. patent application Ser. No. 13/087,203 entitled "System and Method for Registration of Multiple Navigation Systems to a Common Coordinate Frame" filed on 14 Apr. 2011, which is hereby incorporated by reference in its entirety as though fully set forth herein.

The entire disclosure of PCT Application No. PCT/IB2017/050419 entitled "System, Apparatus, and Method of Magnetic Field Distortion Detection in a Magnetic Medical Mapping System" filed on 26 Jan. 2017, which is hereby incorporated by reference in its entirety as though fully set forth herein.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Various modules or other circuits may be implemented to carry out one or more of the operations and activities described herein and/or shown in the figures. In these contexts, a "module" is a circuit that carries out one or more of these or related operations/activities (e.g., processing circuitry, magnetic field generator circuitry, and signal conditioning circuitry). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system to detect and correct for magnetic distortion in a magnetic field for localizing a medical device positioned within the magnetic field, the system comprising:
   a magnetic field emitter including one or more emitter coils at known positions and orientations within the system, each of the one or more emitter coils configured and arranged to emit the magnetic field;
   one or more sensor coils, each of the one or more sensor coils configured and arranged to sense the magnetic field, and output a first electrical signal indicative of the sensed magnetic field at the medical device;
   an array of magnetic distortion sensors at known positions and orientations within the system, each of the magnetic distortion sensors in the array configured and arranged to sense the magnetic field, and output a second electrical signal indicative of the sensed magnetic field at the respective magnetic distortion sensor; and
   processor circuitry communicatively coupled to each of the magnetic distortion sensors and the one or more sensor coils, and configured and arranged to
   receive the first and second electrical signals, and
   determine a magnetic distortion corrected position of the medical device within the system based on the first and second electrical signals by
      determining perceived locations of each of the magnetic distortion sensors in the array based on the sensed magnetic field at each of the magnetic distortion sensors,
      determining a localized error between the perceived location and the known position of each of the magnetic distortion sensors,
      calculating a transform, based on the localized error determinations, that converts the perceived locations to the known position for each of the magnetic distortion sensors, and using the calculated transform, and
   group the perceived locations of the magnetic distortion sensors and determine a gradient of deformation for the group,
   based on the localized error and the determined gradient of deformation for the group, calculate an enhanced transform with spline smoothing, and
   using the enhanced transform to compensate for non-linear deformation at mid-points between the known positions of the group based at least in part on the determined gradient of deformation for the group.

2. The system of claim 1,
   wherein the enhanced transform sets the corrected position at one of the array of magnetic distortion sensors and the gradient is set by a subset of the array of magnetic distortion sensors, and
   wherein the spline smoothing utilizes points of the subset of the array of magnetic distortion sensors to improve interpolation accuracy of the corrected position of the medical device.

3. The system of claim 1, wherein, in response to the localized error exceeding a threshold amount, the processor circuitry is configured and arranged to disregard a perceived medical device position calculated when the localized error exceeds the threshold amount.

4. The system of claim 1, wherein, in response to the localized error exceeding a threshold amount, the processor circuitry outputs a sensory indication to a clinician of the magnetic distortion.

5. The system of claim 1, wherein the transform allows for local warping by applying the following mapping:

$$f: R^3 \Rightarrow R^3$$

such that for each fiducial point pair $s_i=(x_i, y_i)$, the error defined as:

$$e_i = |f(x_i) - y_i|$$

is driven to zero for each fiducial point,
   where $(x_i, y_i)$ is the cartesian coordinates of a particular fiducial point pair, and the subscript i identifies the particular fiducial point pair.

6. The system of claim 1, wherein the transform is calculated using a thin plate spline where a solution is a sum of a set of weighted basis functions centered at each control point, where the weighted basis function is:

$$r^2 \log r, \text{ for the case of } f: R^2 \Rightarrow R^3,$$

and $$r, \text{ for the case of } f: R^3 \Rightarrow R^3,$$

where r is a radial distance of an input point from the particular weighted basis function's center.

7. The system of claim 1, wherein the localized error between the perceived location and the known position for each magnetic distortion sensor of the array is indicative of an error in the perceived location of the medical device within the system.

8. The system of claim 1, wherein the known position of a first magnetic distortion sensor is a perceived location of the first magnetic distortion sensor at a time, T0, and the localized error is determined between the known position at T0 for the first magnetic distortion sensor and the perceived location of the first magnetic distortion sensor at a time, T1, different from the time T0.

9. The system of claim 1, wherein the magnetic field emitter is configured and arranged to generate multiple unique magnetic fields from each of the one or more emitter coils using time multiplexing, frequency multiplexing, or a combination thereof.

10. A computer program for correcting magnetic distortion in a magnetic field for localization of a medical device within a patient, the computer program embodied on a non-transitory computer readable medium and comprising:
   calculating a perceived location of each of a plurality of sensor coils in a sensor array based upon a received signal at each of the plurality of sensor coils indicative of the magnetic field proximate the respective sensor coil;
   determining a positional error of each of the plurality of sensor coils indicative of a magnetic distortion in the magnetic field at each of the respective sensor coils, based on a discrepancy between a known position of each of the respective sensor coils and the perceived location of each of the respective sensor coils;
   computing a transform, based on the discrepancy between the known position and perceived locations of each of the plurality of sensor coils, that converts the perceived location to the known position for each of the plurality of sensor coils;
   calculating a perceived location of the medical device based upon a received signal at the medical device indicative of the magnetic field proximate the medical device; and
   determining an actual location of the medical device by entering the perceived location of the medical device into the computed transform;

wherein the transform is calculated using a thin plate spline where the solution is a sum of a set of weighted basis functions centered at each control point, where the weighted basis function is:

$r^2 \log r$, for the case of $f: R^2 \Rightarrow R^1$ and $r$, for the case of $f: R^3 \Rightarrow R^3$, where r is a radial distance of an input point from the particular weighted basis function's center.

11. The computer program of claim 10 further including:
determining gradients of deformation in the magnetic field by grouping the perceived locations of the plurality of sensor coils; and
wherein the determined gradients of deformation act as a spline smoother in the computed transform.

12. The computer program of claim 10, wherein the transform is based upon a perceived location of each of the plurality of sensor coils at a first time, T0, and each of the plurality of sensor coils respective known position.

13. The computer program of claim 12 further including:
calculating a perceived location of each of the plurality of sensor coils at a second time, T1, based upon a received signal at the sensor coil indicative of the magnetic field at time T1;
computing a second transform to convert the perceived locations of each of the plurality of sensor coils at the time T1 to the plurality of sensors coils perceived location at T0;
calculating a perceived location of the medical device at the time T1, based upon a received signal at the medical device indicative of the magnetic field at time T0; and
determining the actual location of the medical device at time T1 by entering the perceived location of the medical device at time T1 through the second computed transform.

14. The computer program of claim 10, wherein the transform allows for local warping by applying the following mapping:

$f: R^3 \Rightarrow R^3$ such that for each fiducial point pair $s_i \equiv (x_i, y_i)$, the error defined as:

$e_i \equiv |f(x_i) - y_i|$ is driven to zero for each fiducial point,
where $(x_i, y_i)$ is the cartesian coordinates of a particular fiducial point pair, and the subscript i identifies the particular fiducial point pair.

* * * * *